(12) United States Patent
Sheldon et al.

(10) Patent No.: US 10,773,086 B2
(45) Date of Patent: Sep. 15, 2020

(54) IMPLANTABLE MEDICAL DEVICE AND METHOD FOR DETERMINING HIS BUNDLE PACING CAPTURE

(71) Applicant: Medtronic, Inc., Minneapolis, MN (US)

(72) Inventors: Todd J. Sheldon, North Oaks, MN (US); Shawn M. Campbell, Davidson, NC (US); Maureen E. Lybarger, New Brighton, MN (US); Elizabeth A. Mattson, Eagen, MN (US); Eric R. Williams, Maple Grove, MN (US); Zhongping Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 125 days.

(21) Appl. No.: 16/183,867

(22) Filed: Nov. 8, 2018

(65) Prior Publication Data
US 2019/0134404 A1    May 9, 2019

Related U.S. Application Data

(60) Provisional application No. 62/583,082, filed on Nov. 8, 2017, provisional application No. 62/663,619, filed on Apr. 27, 2018.

(51) Int. Cl.
*A61N 1/37* (2006.01)
*A61N 1/378* (2006.01)
(Continued)

(52) U.S. Cl.
CPC ............ *A61N 1/371* (2013.01); *A61B 5/046* (2013.01); *A61B 5/0464* (2013.01); *A61B 5/0472* (2013.01); *A61B 5/4836* (2013.01); *A61B 5/686* (2013.01); *A61N 1/365* (2013.01); *A61N 1/3714* (2013.01); *A61N 1/3787* (2013.01); *A61N 1/37223* (2013.01); *A61N 1/37247* (2013.01); *A61N 1/3956* (2013.01); *A61B 5/042* (2013.01); *A61N 1/3756* (2013.01)

(58) Field of Classification Search
None
See application file for complete search history.

(56) References Cited

U.S. PATENT DOCUMENTS 4,505,276 A    3/1985   Markowitz et al.
6,408,210 B1   6/2002   Bornzin et al.
(Continued)

FOREIGN PATENT DOCUMENTS

EP    1234597    8/2002

OTHER PUBLICATIONS

Deshmukh et al., "Permanent, Direct HIS-Bundle Pacing: A Novel Approach to Cardiac Pacing in Patients with Normal HIS-Purkinje Activation", Circulation, American Heart Association, Inc., vol. 101, No. 8, Feb. 29, 2000, 9 pages.
(Continued)

*Primary Examiner* — Ankit D Tejani

(57) ABSTRACT

An IMD system receives a near field His bundle electrical signal produced by a patient's heart via a first sensing electrode vector and a far field cardiac electrical signal via a second sensing electrode vector different than the first sensing electrode vector. The IMD system generates His bundle pacing pulses delivered to the patient's heart via a His pacing electrode vector and determines a type of cardiac capture evoked by a His bundle pacing pulse.

39 Claims, 10 Drawing Sheets

(51) Int. Cl.
*A61N 1/39* (2006.01)
*A61N 1/372* (2006.01)
*A61B 5/0472* (2006.01)
*A61B 5/046* (2006.01)
*A61B 5/0464* (2006.01)
*A61B 5/00* (2006.01)
*A61N 1/365* (2006.01)
*A61N 1/375* (2006.01)
*A61B 5/042* (2006.01)

(56) References Cited

U.S. PATENT DOCUMENTS

| | | |
|---|---|---|
| 6,768,924 B2 | 7/2004 | Ding et al. |
| 8,155,741 B2 | 4/2012 | Bohn et al. |
| 8,565,880 B2 | 10/2013 | Dong et al. |
| 8,761,880 B2 | 6/2014 | Maskara et al. |
| 9,168,382 B2 | 10/2015 | Shuros et al. |
| 9,227,073 B2 | 1/2016 | Bohn et al. |
| 2011/0264158 A1 | 10/2011 | Dong et al. |
| 2012/0101542 A1 | 4/2012 | Arcot-Krishnamurthy et al. |
| 2014/0107724 A1 | 4/2014 | Shuros et al. |

OTHER PUBLICATIONS (PCT/US2018/059770) PCT Notification of Transmittal of the International Search Report and the Written Opinion of the International Searching Authority, dated Feb. 11, 2019, 13 pages.

Adachi et al, "QRS Complex Widening Due to Loss of Left Bundle Branch Capture: Pitfall of Para-Hisian Pacing", Journal of Interventional Cardiac Electrophysiology 2009, 4 pages.

Yuyun et al., "HIS Bundle Pacing: State of the Art", US Cardiology, vol. 12, No. 1, Jan. 2017, 10 pages.

(PCT/US2018/059766) PCT Notification of Transmittal of the International Search Report and the Written Opinion of the International Searching Authority, dated Jan. 24, 2019, 14 pages.

Dandamudi et al., "How to Perform Permanent His Bundle Pacing in Routine Clinical Practice", 2016, Heart Rhythm Society, 5 pages.

IMPLANTABLE MEDICAL DEVICE AND METHOD FOR DETERMINING HIS BUNDLE PACING CAPTURE

REFERENCE TO RELATED APPLICATIONS

This application claims the benefit of U.S. Patent Application No. 62/583,082, filed provisionally on Nov. 8, 2017, and the benefit of U.S. patent application No. 62/663,619, filed provisionally on Apr. 27, 2018, both of which are incorporated herein by reference in their entirety.

TECHNICAL FIELD

This disclosure relates to an implantable medical device and method for determining capture of the His bundle during cardiac pacing.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (AV) node. The AV node responds by propagating a ventricular depolarization signal through the bundle of His of the ventricular septum and thereafter to the bundle branches and the Purkinje muscle fibers of the right and left ventricles.

Patients with a conduction system abnormality, e.g., poor AV node conduction or poor SA node function, may receive a pacemaker to restore a more normal heart rhythm and AV synchrony. Ventricular pacing may be performed to maintain the ventricular rate in a patient having atrioventricular conduction abnormalities. A single chamber ventricular pacemaker may be coupled to a transvenous ventricular lead carrying electrodes placed in the right ventricle, e.g., in the right ventricular apex. The pacemaker itself is generally implanted in a subcutaneous pocket with the transvenous ventricular lead tunneled to the subcutaneous pocket. Intracardiac pacemakers have been introduced or proposed for implantation entirely within a patient's heart, eliminating the need for transvenous leads. An intracardiac pacemaker may provide sensing and pacing from within a chamber of the patient's heart, e.g., from within the right ventricle in a patient having AV conduction block.

Dual chamber pacemakers are available which include a transvenous atrial lead carrying electrodes which are placed in the right atrium and a transvenous ventricular lead carrying electrodes that are placed in the right ventricle via the right atrium. A dual chamber pacemaker senses atrial electrical signals and ventricular electrical signals and can provide both atrial pacing and ventricular pacing as needed to promote a normal atrial and ventricular rhythm and promote AV synchrony when SA and/or AV node or other conduction abnormalities are present.

Cardiac pacing of the His bundle has been proposed to provide ventricular pacing along the heart's natural conduction system. Ventricular pacing at the right ventricular apex has been found to be associated with increased risk of atrial fibrillation and heart failure. Alternative pacing sites have been investigated or proposed, such as pacing of the His bundle. Pacing the ventricles via the His bundle allows recruitment along the heart's natural conduction system, including the Purkinje fibers, and is hypothesized to promote more physiologically normal electrical and mechanical synchrony than other pacing sites, such as the ventricular apex.

SUMMARY

The techniques of this disclosure generally relate to determining the type of capture achieved by cardiac pacing pulses delivered via His bundle pacing electrodes. The pacing electrodes may be carried by a lead, e.g., a transvenous endocardial lead or be carried by the housing of a leadless pacemaker. Among the types of capture that may be achieved during His bundle pacing are selective His bundle capture, non-selective His bundle capture, ventricular myocardial capture, atrial capture, and loss of ventricular capture. The type of capture may depend on the location of the electrodes relative to the His bundle, the pacing pulse energy and other factors. An implantable medical device (IMD) operating according to the techniques disclosed herein may determine the type of capture following a His bundle pacing pulse, determine various capture thresholds for different types of capture such as selective and non-selective His bundle capture, and select pacing pulse control parameters such as pacing pulse amplitude based on the determined capture type and capture thresholds. The IMD may be configured to monitor for capture during His bundle pacing to detect a change in capture type and provide an appropriate response.

In one example, the disclosure provides IMD system including a sensing circuit, a therapy delivery circuit and a control circuit coupled to the sensing circuit and the therapy delivery circuit. The sensing circuit is configured to receive a near field His bundle electrical signal via a first sensing electrode vector and receive a far field cardiac electrical signal via a second sensing electrode vector different than the first sensing electrode vector. The therapy delivery circuit is configured to generate His bundle pacing pulses delivered to a patient's heart via a His pacing electrode vector. The control circuit is configured to determine a type of cardiac capture evoked by a His bundle pacing pulse delivered by the therapy delivery circuit. Determining the type of capture may include detecting a near field QRS signal from the near field His bundle electrical signal following the His bundle pacing pulse; determining a time interval from the His bundle pacing pulse to the near field QRS signal and comparing the time interval to a time interval threshold. In response to the time interval being less than the time interval threshold, the control circuit may determine a feature of the far field cardiac electrical signal, compare the far field cardiac electrical signal feature to a non-selective His bundle capture threshold, and determine the type of cardiac capture as being non-selective His bundle capture that includes capture of both the His bundle and ventricular myocardium in response to at least the far field cardiac electrical signal feature being less than the non-selective His bundle capture threshold. The control circuit may determine the type of cardiac capture as being only ventricular myocardial capture in response to at least the far field cardiac electrical signal feature being greater than the non-selective His bundle capture threshold.

In another example, the disclosure provides a method performed by an IMD including receiving by a sensing circuit of an implantable medical device a near field His bundle electrical signal via a first sensing electrode vector, receiving a far field cardiac electrical signal by the sensing circuit via a second sensing electrode vector different than the first sensing electrode vector and generating His bundle pacing pulses delivered to a patient's heart via a His pacing electrode vector. The method further includes determining a type of cardiac capture evoked by a His bundle pacing pulse delivered by the therapy delivery circuit. Determining the type of cardiac capture may include detecting a near field QRS signal from the near field His bundle electrical signal following the His bundle pacing pulse, determining a time interval from the His bundle pacing pulse to the near field QRS signal and comparing the time interval to a time interval threshold. In response to the time interval being less than the time interval threshold, the method may include determining a feature of the far field cardiac electrical signal, comparing the far field cardiac electrical signal feature to a non-selective His bundle capture threshold. The method may further include determining the type of cardiac capture as being non-selective His bundle capture that includes capture of both of the His bundle and ventricular myocardium of the patient's heart in response to at least the far field cardiac electrical signal feature being less than the non-selective His bundle capture threshold and determining the type of cardiac capture as being only ventricular myocardial capture in response to at least the far field cardiac electrical signal feature being greater than the non-selective His bundle capture threshold.

In yet another example, the disclosure provides a non-transitory, computer-readable storage medium comprising a set of instructions which, when executed by a controller of an IMD, cause the IMD to receive a near field His bundle electrical signal produced by a patient's heart via a first sensing electrode vector, receive a far field cardiac electrical signal produced by the patient's heart via a second sensing electrode vector different than the first sensing electrode vector, generate His bundle pacing pulses delivered to the patient's heart via a His pacing electrode vector, and determine a type of cardiac capture evoked by a delivered His bundle pacing pulse. The type of cardiac capture may be determined by detecting a near field QRS signal from the near field His bundle signal following the His bundle pacing pulse, determining a time interval from the His bundle pacing pulse to the near field QRS signal, comparing the time interval to a time interval threshold, in response to the time interval being less than the time interval threshold, determining a feature of the far field cardiac electrical signal and comparing the far field cardiac electrical signal feature to a non-selective His bundle capture threshold. Determining the type of cardiac capture may further include determining the type of cardiac capture as being non-selective His bundle capture that includes capture of both the His bundle and ventricular myocardium in response to at least the far field cardiac electrical signal feature being less than the non-selective His bundle capture threshold and determining the type of cardiac capture as being ventricular myocardial capture in response to at least the far field cardiac electrical signal feature being greater than the non-selective His bundle capture threshold.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

An IMD capable of delivering His bundle pacing and detecting and monitoring capture of the His bundle is described herein. A heart chamber is "captured" by a pacing pulse having sufficient electrical energy to cause depolarization of the cardiac tissue, causing an electrical "evoked response," and subsequent mechanical contraction of the heart chamber. In order to effectively capture and pace the heart to achieve a desired therapeutic effect, cardiac pacing pulses need to have a pulse energy that is equal to or greater than the capture threshold of the cardiac tissue at the pacing site. A pacing capture threshold test may be performed to determine the minimum pacing pulse amplitude for a given pacing pulse width (or vice versa) that captures the heart chamber. Determination of the capture threshold enables proper programming of the pacing pulse amplitude and pulse width to promote effective pacing and avoid loss of capture. Capture monitoring by the pacemaker allows automatic adjustments to the pacing pulse amplitude and/or width to a suprathreshold value when loss of capture is detected.

When pacing pulses are delivered by electrodes positioned in the heart to pace the His bundle, it is possible to capture only the His bundle tissue, capture both the His bundle and surrounding ventricular myocardium, or capture the surrounding ventricular myocardium without capturing the His bundle. Capture of only the His bundle is referred to herein as "selective" His bundle (SHB) capture. Capture of the His bundle and surrounding ventricular myocardial tissue is referred to herein as "non-selective" His bundle (NSHB) capture. Capture of the surrounding ventricular myocardium without capturing the His bundle is referred to as ventricular myocardial (VM) capture. In some instances, capture of only the right bundle branch may occur in response to an intended His bundle pacing pulse, atrial capture may occur instead of His bundle or ventricular myocardial capture, or fusion may occur when pacing pulse capture and an intrinsic depolarization occur simultaneously. Determination of which type of capture is occurring in response to an intended His bundle pacing pulse and determination of the His bundle capture threshold allows for providing selective or non-selective pacing of the His bundle in order to achieve pacing along the native ventricular conduction system.

Figure 1:
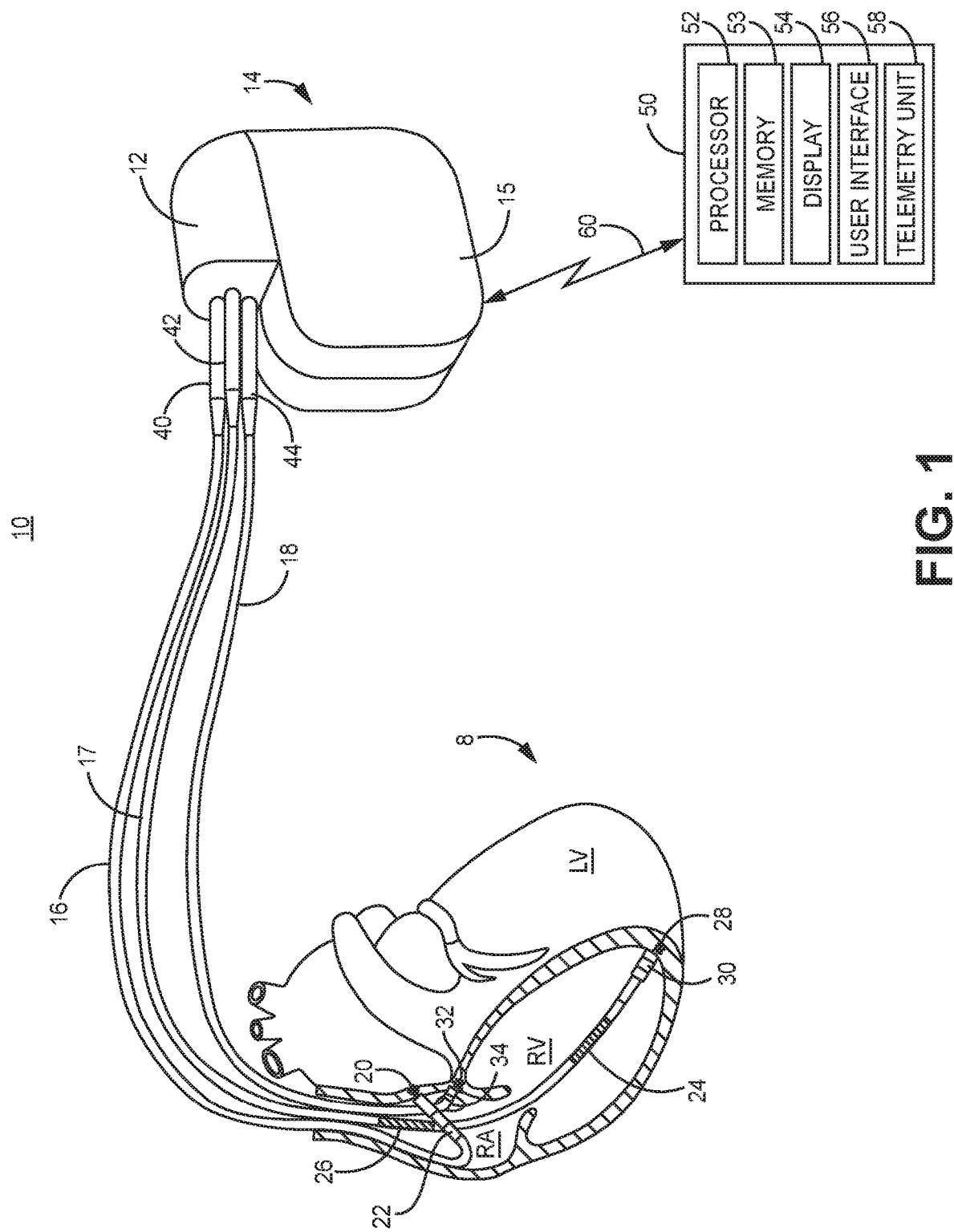
FIG. 1 is a conceptual diagram of an IMD system capable of pacing and sensing in a patient's heart.

FIG. 1 is a conceptual diagram of an IMD system 10 capable of pacing and sensing in a patient's heart 8. The IMD system 10 includes IMD 14 coupled to a patient's heart 8 via transvenous electrical leads 16, 17 and 18. IMD 14 is shown as a dual chamber device capable of delivering cardiac pacing pulses and sensing cardiac electrical signals in the right atrium (RA) and in the right ventricle (RV). Housing 15 encloses internal circuitry corresponding to the various circuits and components described in conjunction with FIG. 3 below, for sensing cardiac signals from heart 8, detecting arrhythmias, controlling therapy delivery and monitoring His bundle capture using the techniques disclosed herein.

IMD 14 includes a connector block 12 that may be configured to receive the proximal ends of a RA lead 16, RV lead 17 and a His lead 18, which are advanced transvenously for positioning electrodes for sensing and stimulation in the RA and RV. RA lead 16 is positioned such that its distal end is in the vicinity of the right atrium and the superior vena cava. RA lead 16 is equipped with pacing and sensing electrodes 20 and 22, shown as a tip electrode 20 and a ring electrode 22 spaced proximally from tip electrode 20. The electrodes 20 and 22 provide sensing and pacing in the right atrium and are each connected to a respective insulated conductor extending within the elongated body of RA lead 16. Each insulated conductor is coupled at its proximal end to a connector carried by proximal lead connector 40.

His lead 18 is advanced within the right atrium to position electrodes 32 and 34 for pacing and sensing in the vicinity of the His bundle. His lead tip electrode 32 may be a helical electrode that is advanced into the inferior end of the interatrial septum, beneath the AV node and near the tricuspid valve annulus to position tip electrode 32 in or proximate to the His bundle. A ring electrode 34 spaced proximally from tip electrode 32 may be used as the return electrode with the cathode tip electrode 32 for pacing the right and left ventricles via the native ventricular conduction system extending from the His bundle. An intracardiac electrogram (EGM) signal may be produced by IMD 14 from the cardiac electrical signal obtained using the tip electrode 32 and ring electrode 34 of His lead 18 and received by sensing circuitry included in IMD 14. As described below, the EGM signal produced from the cardiac electrical signal received via His lead 18 may be used for detecting capture of the His bundle and discriminating between SHB capture, NSHB capture, VM capture and loss of capture. The electrodes 32 and 34 are coupled to respective insulated conductors extending within the elongated body of His lead 18, which provide electrical connection to the proximal lead connector 44 coupled to connector block 12.

In some examples, IMD 14 may optionally be coupled to RV lead 17 for positioning electrodes within the RV for sensing RV cardiac signals and delivering pacing or shocking pulses in the RV. For these purposes, RV lead 17 is equipped with pacing and sensing electrodes shown as a tip electrode 28 and a ring electrode 30. RV lead 17 is further shown to carry defibrillation electrodes 24 and 26, which may be elongated coil electrodes used to deliver high voltage CV/DF pulses. Defibrillation electrode 24 may be referred to as the "RV defibrillation electrode" or "RV coil electrode" because it may be carried along RV lead 17 such that it is positioned substantially within the right ventricle when distal pacing and sensing electrodes 28 and 30 are positioned for pacing and sensing in the right ventricle. Defibrillation electrode 26 may be referred to as a "superior vena cava (SVC) defibrillation electrode" or "SVC coil electrode" because it may be carried along RV lead 17 such that it is positioned at least partially along the SVC when the distal end of RV lead 17 is advanced within the right ventricle.

Each of electrodes 24, 26, 28 and 30 are connected to a respective insulated conductor extending within the body of RV lead 17. The proximal end of the insulated conductors are coupled to corresponding connectors carried by proximal lead connector 42, e.g., a DF-4 connector, for providing electrical connection to IMD 14. In other examples, RV lead 17 may carry RV coil electrode 24 and SVC coil electrode 26 to provide high voltage therapies without carrying any pacing and sensing electrodes 28 and 30. Housing 15 may function as an active electrode during CV/DF shock delivery in conjunction with RV coil electrode 24 or SVC coil electrode 26. In some examples, housing 15 may function as a return electrode for unipolar sensing or pacing configurations with any of the electrodes carried by leads 16, 17 and 18.

It is to be understood that although IMD 14 is illustrated in FIG. 1 as an implantable cardioverter defibrillator capable of delivering both low voltage cardiac pacing therapies and high voltage cardioversion and defibrillation (CV/DF) shocks, IMD 14 may be configured as a dual-chamber pacemaker in other examples coupled to only RA lead 16 and His lead 18 without having CV/DF shock delivery capabilities and without being coupled to a third lead, such as RV lead 17. In still other examples, IMD 14 may be a single chamber device coupled only to His lead 18 for delivering pacing pulses to the ventricles for at least maintaining a minimum ventricular rate.

An external device 50 is shown in telemetric communication with IMD 14 by a communication link 60. External device 50 may include a processor 52, memory 53, display unit 54, user interface 56 and telemetry unit 58. Processor 52 controls external device operations and processes data and signals received from IMD 14. Display unit 54, which may include a graphical user interface, displays data and other information to a user for reviewing IMD operation and programmed parameters as well as cardiac electrical signals retrieved from IMD 14. Data obtained from IMD 14 via communication link 60 may be displayed on display 54. For example, a clinician may view cardiac electrical signals received from IMD 14 and/or results of His capture threshold testing and monitoring or data derived therefrom.

User interface 56 may include a mouse, touch screen, key pad or the like to enable a user to interact with external device 50 to initiate a telemetry session with IMD 14 for retrieving data from and/or transmitting data to IMD 14, including programmable parameters for controlling His capture determination as described herein. Telemetry unit 58 includes a transceiver and antenna configured for bidirectional communication with a telemetry circuit included in IMD 14 and is configured to operate in conjunction with processor 52 for sending and receiving data relating to IMD functions via communication link 60, which may include data relating to His bundle and ventricular capture management, such as capture thresholds determined for SHB capture, NSHB capture and VM capture.

Communication link 60 may be established between IMD 14 and external device 50 using a wireless radio frequency (RF) link such as BLUETOOTH®, Wi-Fi, or Medical Implant Communication Service (MICS) or other RF or communication frequency bandwidth or communication protocols. Data stored or acquired by IMD 14, including physiological signals or associated data derived therefrom, results of device diagnostics, and histories of detected rhythm episodes and delivered therapies, may be retrieved from IMD 14 by external device 50 following an interrogation command.

External device 50 may be embodied as a programmer used in a hospital, clinic or physician's office to retrieve data from IMD 14 and to program operating parameters and algorithms in IMD 14 for controlling IMD functions. External device 50 may alternatively be embodied as a home monitor or hand held device. External device 50 may be used to program cardiac signal sensing parameters, cardiac rhythm detection parameters and therapy control parameters used by IMD 14. Thresholds or other parameters used for detecting SHB capture, NSHB capture and VM capture according to techniques disclosed herein may be programmed into IMD 14 using external device 50.

Figure 2:
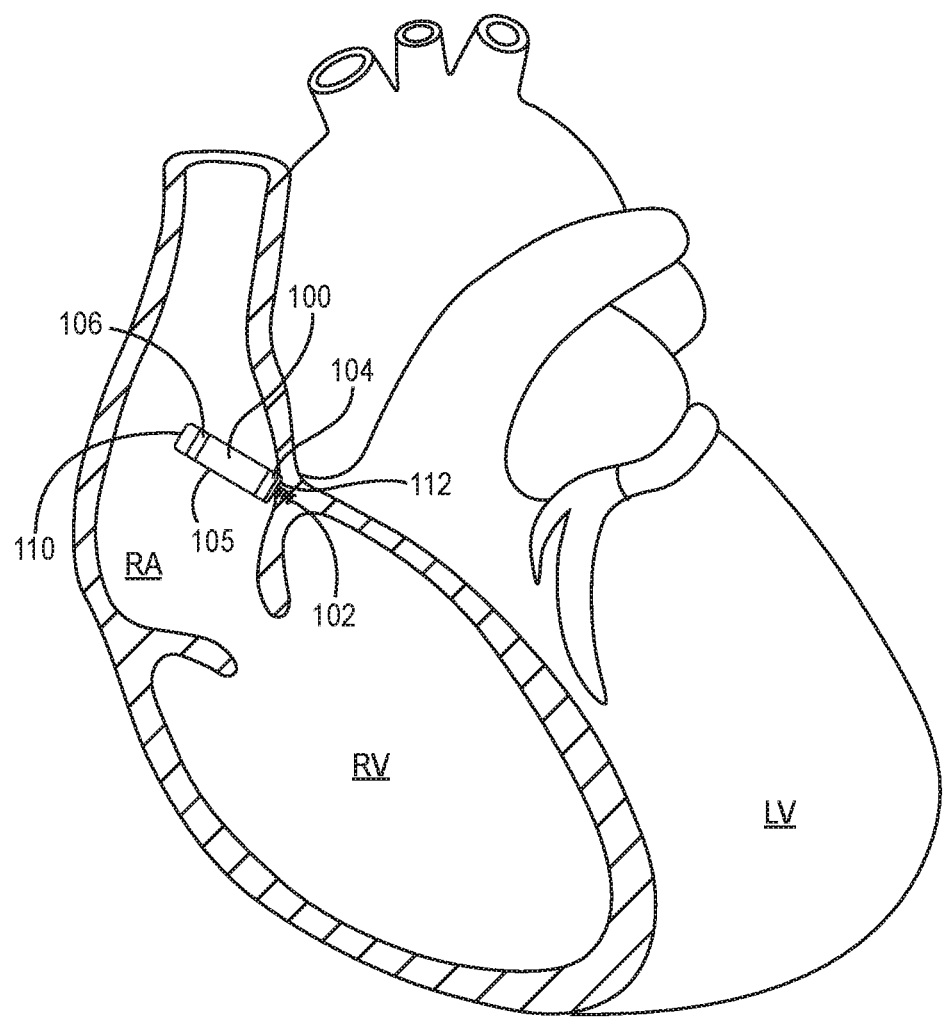
FIG. 2 is a conceptual diagram of a leadless intracardiac pacemaker positioned within the right atrium for providing ventricular pacing.

FIG. 2 is a conceptual diagram of a leadless intracardiac pacemaker 100 positioned within the RA for providing ventricular pacing via the His bundle. Pacemaker 100 may include a distal tip electrode 102 extending away from a distal end 112 of the pacemaker housing 105. Intracardiac pacemaker 100 is shown implanted in the RA of the patient's heart 8 to place distal tip electrode 102 for delivering pacing pulses to the His bundle. For example, the distal tip electrode 102 may be inserted into the inferior end of the interatrial septum, beneath the AV node and near the tricuspid valve annulus to position tip electrode 102 in, along or proximate to the His bundle. Distal tip electrode 102 may be a helical electrode providing fixation to anchor the pacemaker 100 at the implant position. In other examples, pacemaker 100 may include a fixation member that includes one or more tines, hooks, barbs, helices or other fixation member(s) that anchor the distal end of the pacemaker 100 at the implant site.

A portion of the distal tip electrode 102 may be electrically insulated such that only the most distal end of tip electrode 102, furthest from housing distal end 112, is exposed to provide targeted pacing at a tissue site that includes a portion of the His bundle. One or more housing-based electrodes 104 and 106 may be carried on the surface of the housing of pacemaker 100. Pacing of the His bundle may be achieved using the distal tip electrode 102 as the cathode electrode and either of the housing-based electrodes 104 and 106 as the return anode.

Cardiac electrical signals produced by heart 8 may be sensed by pacemaker 100 using a sensing electrode pair selected from electrodes 102, 104 and 106. For example, a near-field signal may be sensed using distal tip electrode 112 and distal housing-based electrode 104. A second electrical signal, which is a relatively more far-field signal, may be sensed using electrodes 104 and 106. The cardiac electrical signals may be analyzed for determining His bundle capture and discriminating between at least SHB capture, NSHB capture and VM capture.

Figure 3:
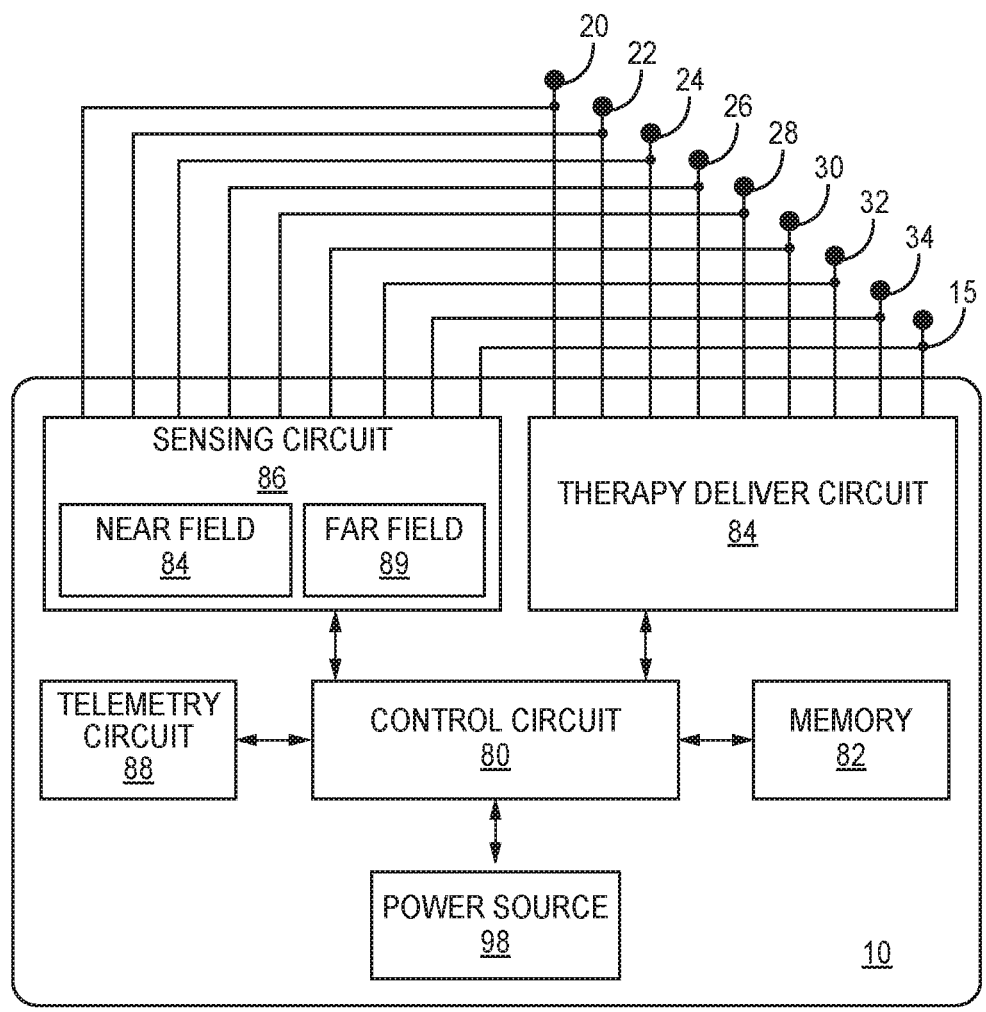
FIG. 3 is a schematic diagram of circuitry that may be enclosed within an IMD configured to perform His bundle pacing and capture detection.

FIG. 3 is a schematic diagram of circuitry that may be enclosed within an IMD configured to perform His bundle pacing and capture detection. The block diagram of FIG. 3 represents IMD 10 for the sake of illustration but it is to be understood that the functionality attributed to the various circuits and components shown in FIG. 3 for performing His bundle pacing and detection and discrimination of SHB, NSHB and VM capture among other types of capture and/or loss of capture may be similarly implemented in the intracardiac pacemaker 100 of FIG. 2 or other IMDs capable of delivering His pacing pulses and sensing cardiac electrical signals. Housing 15 is represented as an electrode in FIG. 3 for use in sensing and cardiac electrical stimulation pulse delivery. The electronic circuitry enclosed within housing 15 includes software, firmware and hardware that cooperatively monitor electrical cardiac signals, determine when a pacing therapy is necessary, and deliver electrical pacing pulses to the patient's heart as needed according to programmed pacing mode and pacing pulse control parameters. The electronic circuitry includes a control circuit 80, memory 82, therapy delivery circuit 84, sensing circuit 86, telemetry circuit 88 and power source 98.

Power source 98 provides power to the circuitry of IMD 10 including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86, and 88 are to be understood from the general block diagram of FIG. 3, but are not shown for the sake of clarity. For example, power source 98 may be coupled to one or more charging circuits included in therapy delivery circuit 84 for providing the power needed to charge holding capacitors included in therapy delivery circuit 84 that are discharged at appropriate times under the control of control circuit 80 for delivering pacing pulses. Power source 98 is also coupled to components of sensing circuit 86, such as sense amplifiers, analog-to-digital converters, switching circuitry, etc., telemetry circuit 88 and memory 82 to provide power to the various circuits as needed.

The functional blocks shown in FIG. 3 represent functionality included in IMD 10 and may include any discrete and/or integrated electronic circuit components that implement analog and/or digital circuits capable of producing the functions attributed to IMD 10 (or pacemaker 100) herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. Providing software, hardware, and/or firmware to accomplish the described functionality in the context of any modern cardiac medical device system, given the disclosure herein, is within the abilities of one of skill in the art.

Control circuit 80 communicates, e.g., via a data bus, with therapy delivery circuit 84 and sensing circuit 86 for sensing cardiac electrical signals and controlling delivery of cardiac electrical stimulation therapies in response to sensed cardiac events, e.g., P-waves and R-waves, or the absence thereof. The available electrodes are electrically coupled to therapy delivery circuit 84 for delivering electrical stimulation pulses to the patient's heart and/or to sensing circuit 86 for sensing cardiac electrical signals produced by the heart, including both intrinsic signals produced by the heart in the absence of a stimulation pulse and evoked response signals produced by the heart in response to a delivered stimulation pulse.

Sensing circuit 86 may include two or more sensing channels for sensing cardiac electrical signals from two or more sensing electrode vectors. For example, a RA signal may be sensed using electrodes 20 and 22, an RV signal may be sensed using electrodes 28 and 30, and a His signal may be sensed using electrodes 32 and 34. As described below, a His bundle near field signal may be sensed by one sensing channel, shown as near field sensing channel 84, for example using electrodes 32 and 34 of His lead 18. A far field signal may be sensed by a second sensing channel, shown as far field sensing channel 89.

As used herein, a "near field" signal refers to a cardiac electrical signal received from a sensing electrode vector including at least one electrode positioned in or proximate to the His bundle, in the vicinity of the site of His pacing pulse delivery, such that the near field signal may also be referred to as a "His bundle near field signal." The His bundle near field signal may or may not include a His bundle evoked response depending on whether the His bundle was captured or not. The His bundle near field signal may include an evoked response signal caused by SHB capture, an evoked response signal caused by NSHB capture or an evoked response signal caused by VM capture.

As used herein, a "far field" signal refers to a cardiac electrical signal received from a sensing electrode vector that is relatively further away from the His bundle than the electrode vector used to sense the His bundle near field signal and/or has a greater inter-electrode distance between the two electrodes defining the far field sensing electrode vector than the inter-electrode distance between the two electrodes defining the His bundle near field sensing electrode vector. The far field signal is more representative of the global activation of the ventricles as opposed to the near field signal being more representative of local tissue activation at or near the pacing site. The far field signal may include an evoked response signal associated with SHB capture, NSHB capture or VM capture. When the His bundle is captured, either selectively or non-selectively, the far field QRS width is narrower than when the His bundle is not captured (and the ventricular myocardial tissue is captured instead).

In some examples, the far field signal may be sensed using an electrode carried by RA lead 16 and the IMD housing 15, e.g., electrode 20 and housing 15 or electrode 22 and housing 15. In examples that include RV lead 17, the far field signal may be sensed using RV coil electrode 24 paired with housing 15, SVC coil electrode 26 paired with housing 15, or RV coil electrode 24 paired with SVC coil electrode 26. The His bundle capture detection methods disclosed herein include detecting SHB capture from the near field signal and discriminating between NSHB capture and VM capture from the far field signal when SHB capture is not detected.

Sensing circuit 86 may include switching circuitry for selectively coupling a near field sensing electrode pair from the available electrodes to the near field sensing channel 87 for sensing a near field His bundle signal and for selectively coupling a far field sensing electrode pair to far field sensing channel 89 for sensing an electrical signal that is far field relative to the site of delivering His bundle pacing pulses. The far field sensing electrode pair may exclude at least one or both of the electrodes used to deliver the His bundle pacing pulses. Switching circuitry may include a switch array, switch matrix, multiplexer, or any other type of switching device suitable to selectively couple components of sensing circuit 86 to selected electrodes.

Each of near field sensing channel 87 and far field sensing channel 89 may include an input filter for receiving a cardiac electrical signal from a respective sensing electrode pair, a pre-amplifier, an analog-to-digital converter and a bandpass filter for producing a multi-bit digital EGM signal for use in detecting His bundle capture and discriminating between at least SHB, NSHB, and VM capture and may discriminate between other types of capture, such as right bundle branch capture, and fusion. Features of the near field and far field EGM signals may be determined by control circuit 80, and in some examples each sensing channel 87 and 89 may include a rectifier to produce a rectified signal from which signal features may be determined by control circuit 80 for use in determining His bundle capture. As described below in conjunction with FIGS. 4-6, the QRS signal following a His bundle pacing pulse may be used to detect His bundle pacing pulse capture and discriminate between different types of capture based upon features of the QRS signal in the near field and far field signals. The QRS signal following a His bundle pacing pulse that captures the His bundle and/or the ventricular myocardium may also be referred to herein as an "evoked response signal" and includes the evoked response R-wave that may be sensed by sensing circuit 86.

Sensing circuit 86 may include cardiac event detection circuitry, which may include one or more sense amplifiers, filters, rectifiers, threshold detectors, comparators, analog-to-digital converters (ADCs), timers or other analog or digital components, for detecting cardiac electrical events. For example, an atrial event detector may be included in sensing circuit 86 for detecting intrinsic P-waves attendant to intrinsic atrial depolarizations using one or both of electrodes 20 and 22 carried by RA lead 16. A ventricular event detector may be included in sensing circuit 86 for detecting intrinsic R-waves attendant to intrinsic ventricular depolarizations using electrodes 32 and 34 carried by His lead 18 and/or using electrodes 24, 26, 28 and/or 30 carried by RV lead 17. A cardiac event sensing threshold, such as a P-wave sensing threshold or an R-wave sensing threshold, may be automatically adjusted by sensing circuit 86 under the control of control circuit 80, e.g., based on timing intervals and sensing threshold values determined by control circuit 80, stored in memory 82, and/or controlled by hardware, firmware and/or software of control circuit 80 and/or sensing circuit 86. The R-wave sensing threshold, for example, may be controlled to start at a starting threshold voltage following a post-ventricular blanking period then decrease according to a decay profile until reaching a minimum sensing threshold. The minimum R-wave sensing threshold may be set to a programmed sensitivity of the R-wave detection circuitry in the respective near field sensing channel 84 or in the far field sensing channel 89. The sensitivity, programmed to a voltage level typically in millivolts, is the lowest voltage level above which a cardiac event, an R-wave in this example, can be sensed by the cardiac event detection circuitry. A low sensitivity setting makes sensing circuit 86 more sensitive to detecting a cardiac event, and a high sensitivity setting makes sensing circuit 86 less sensitive to detecting cardiac events.

Upon detecting a cardiac electrical event based on a sensing threshold crossing, sensing circuit 86 may produce a sensed event signal that is passed to control circuit 80. For example, an atrial event detector may produce a P-wave sensed event signal in response to a P-wave sensing threshold crossing. A ventricular event detector may produce an R-wave sensed event signal in response to an R-wave sensing threshold crossing. The sensed event signals are used by control circuit 80 for setting pacing escape interval timers that control the basic time intervals used for scheduling cardiac pacing pulses. Control circuit 80 may include various timers or counters for counting down an atrioventricular (AV) pacing interval, a VV pacing interval, an AA pacing interval, etc. A sensed event signal may trigger or inhibit a pacing pulse depending on the particular programmed pacing mode. For example, a P-wave sensed event signal received from sensing circuit 86 may cause control circuit 80 to inhibit a scheduled atrial pacing pulse and schedule a His bundle pacing pulse at the programmed AV pacing interval. If the AV pacing interval expires before control circuit 80 receives an R-wave sensed event signal from sensing circuit 86, control circuit 80 may control therapy delivery circuit 84 to deliver a His pacing pulse at the AV pacing interval following the sensed P-wave and in this way deliver atrial-synchronized ventricular pacing. If an R-wave sensed event signal is received from sensing circuit 86 before the AV pacing interval expires, the scheduled His pacing pulse may be inhibited. The AV pacing interval controls the amount of time between an atrial event, paced or sensed, and a His bundle pacing pulse to promote AV synchrony.

Therapy delivery circuit 84 may include charging circuitry, one or more charge storage devices such as one or more holding capacitors, an output capacitor, and switching circuitry that controls when the holding capacitor(s) are charged and discharged across the output capacitor to deliver a pacing pulse to a selected pacing electrode vector coupled to the therapy delivery circuit 84. Therapy delivery circuit 84 may include one or more pacing channels. In the example of IMD 10, therapy delivery circuit 84 may include an RA pacing channel, a His pacing channel and an RV pacing channel each including a holding capacitor, one or more switches, and an output capacitor for producing pacing pulses delivered by the respective RA lead 16, RV lead 17 and His lead 18. Charging of a holding capacitor to a programmed pacing voltage amplitude and discharging of the capacitor for a programmed pacing pulse width may be performed by therapy delivery circuit 84 according to control signals received from control circuit 80. For example, a pace timing circuit included in control circuit 80 may include programmable digital counters set by a microprocessor of the control circuit 80 for controlling the basic pacing time intervals associated with various single chamber or dual chamber pacing modes or anti-tachycardia pacing sequences. The microprocessor of control circuit 80 may also set the amplitude, pulse width, polarity or other characteristics of the cardiac pacing pulses, which may be based on programmed values stored in memory 82.

In some examples, IMD 10 may be configured to detect non-sinus tachycardia and deliver anti-tachycardia pacing (ATP). Control circuit 80 may determine cardiac event time intervals, e.g., PP intervals between consecutive P-wave sensed event signals received from sensing circuit 86 and RR intervals between consecutive R-wave sensed event signals received from sensing circuit 86. These intervals may be compared to tachycardia detection intervals for detecting non-sinus tachycardia. Tachycardia may be detected in a given heart chamber based on a threshold number of tachycardia detection intervals being detected. In response to detecting atrial or ventricular tachycardia, control circuit 80 may control therapy delivery circuit 84 to deliver ATP.

Therapy delivery circuit 84 may include high voltage therapy circuitry for generating high voltage shock pulses in addition to low voltage therapy circuitry for generating low voltage pacing pulses. In response to detecting atrial or ventricular tachycardia or fibrillation, control circuit 80 may control therapy delivery circuit 84 to deliver a cardioversion/defibrillation (CV/DF) shock. The high voltage therapy circuitry may include high voltage capacitors and associated charging circuitry for generating and delivering CV/DF shock pulses using coil electrodes 24 and 26 and/or housing 15.

Control parameters utilized by control circuit 80 for sensing cardiac events, and controlling pacing therapy delivery may be programmed into memory 82 via telemetry circuit 88. Telemetry circuit 88 includes a transceiver and antenna for communicating with an external device 50 (FIG. 1) using radio frequency communication or other communication protocols. Under the control of control circuit 80, telemetry circuit 88 may receive downlink telemetry from and send uplink telemetry to the external device 50. In some cases, telemetry circuit 88 may be used to transmit and receive communication signals to/from another medical device implanted in the patient.

Figure 4:
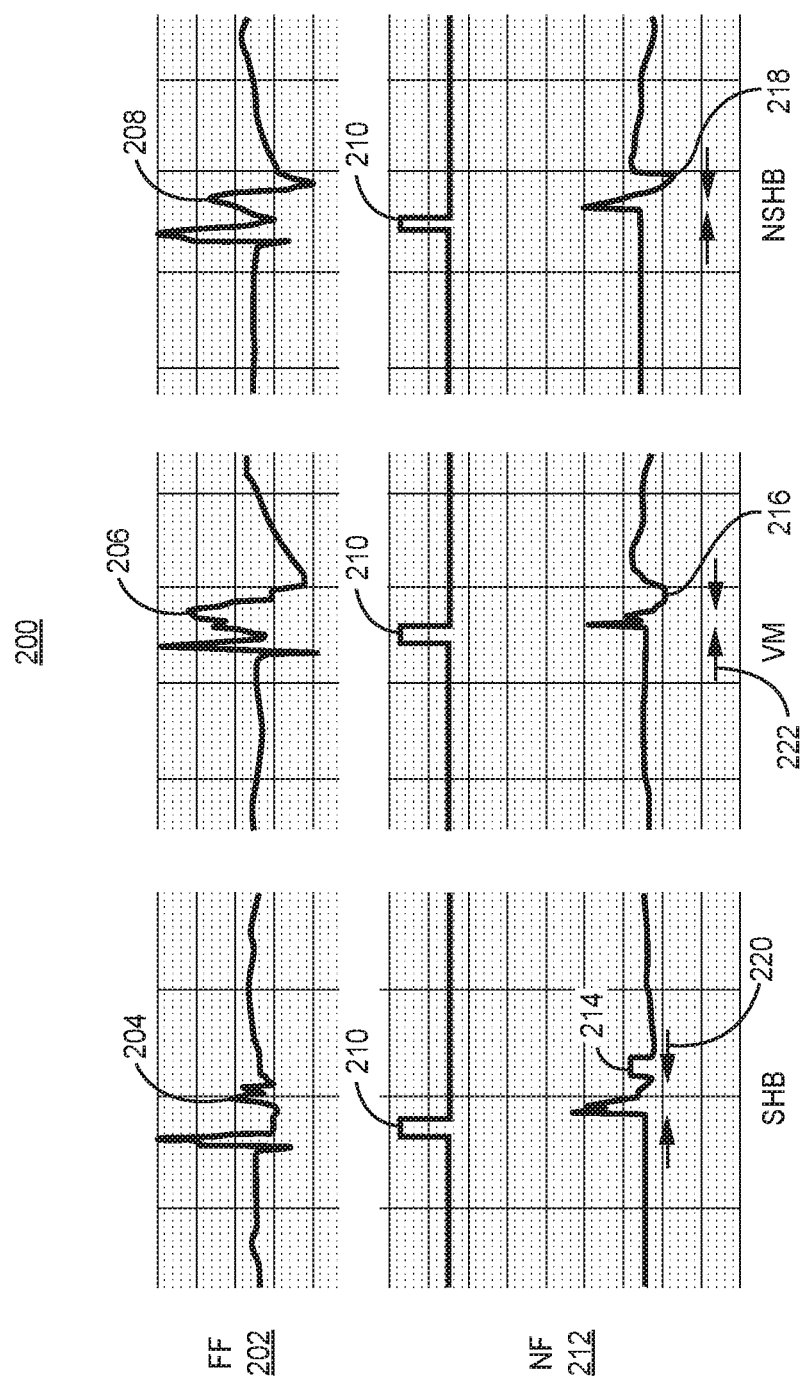
FIG. 4 is a diagram of evoked response signals representing different types of cardiac capture in response to His bundle pacing pulses.

FIG. 4 is a diagram 200 of cardiac electrical signals including evoked response signals representing SHB capture (left column), NSHB capture (right column), and VM capture (center column). Far field cardiac electrical signals 202 and corresponding His bundle near field signals 212 are shown aligned in time with a respective His bundle pacing pulse 210 in each example.

In the left column, the His bundle pacing pulse 210 that results in SHB capture produces a His bundle near field evoked response signal 214 that occurs after a time delay 220. The His bundle near field evoked response signal 214 has a positive polarity and relatively narrow signal width. The far field evoked response signal 204 is also seen to be relatively narrow, positive in polarity and occurring after a time delay. The time delay 220 following the His bundle pacing pulse 210 until the QRS complex (evoked response signal 214) is due to the time required for the depolarization to be conducted along the His Purkinje conduction system.

In the middle column, the far field evoked response signal 206 and the corresponding His bundle near field evoked response signal 216 following a His bundle pacing pulse 210 that only captures ventricular myocardial tissue without capturing the His bundle are shown. The near field evoked response signal 216 occurs after a relatively shorter time delay 222 than the time delay 220 of evoked response signal 214 during SHB capture due to the absence of conduction along the His Purkinje conduction system. The near field evoked response signal 216 during VM capture is relatively wide and has a negative polarity.

The far field evoked response signal 208 and His bundle near field evoked response signal 218 during NSHB capture are shown in the right column. In the His bundle near field signal 212, the VM capture evoked response signal 216 (middle column) and the NSHB evoked response signal 218 are substantially similar. Both signals 216 and 218 occur early after the respective His bundle pacing pulse 210, both are negative in polarity and have similar signal widths, which are relatively wider than the SHB evoked response signal 214. Accordingly, SHB capture may be positively detected from the His bundle near field signal 212, e.g., based on the longer time delay 220 until the evoked response signal 214, the positive polarity (at least in some patients), relatively narrow signal width, relatively small signal waveform area or any combination thereof. The similarities of the timing and morphology of the His bundle near field evoked response signal 218 during NSHB capture and the near field evoked response signal 216 during VM capture makes these two types of capture difficult to distinguish from the His bundle near field signal 212 alone.

The far field evoked response signal 208 during NSHB capture, however, is distinctly narrower than the far field evoked response signal 206 during VM capture. If SHB capture is not positively detected based on a late, narrow and/or positive polarity of near field evoked response signal 214, the type of capture, e.g., either VM capture or NSHB capture, may be determined from a far field signal 202, e.g., based on the far field evoked response signal width, area, and/or QRS waveform morphology. A QRS width, area or waveform template for a known type of capture may be established or determined. For instance, a wavelet transform may be performed on the QRS waveform of an unknown type of capture to produce wavelet coefficients that are compared to wavelet coefficients of a known capture template. Known capture templates may be generated for SHB capture, NSHB capture and/or VM capture. A template comparison to an unknown QRS waveform may be used to determine the capture type during His pacing capture monitoring. A QRS template comparison of either the His bundle near field and/or far field signal may be performed alone or in combination with comparisons of the QRS width and/or QRS area to respective thresholds for determining the type of capture achieved by a His bundle pacing pulse.

Figure 5:
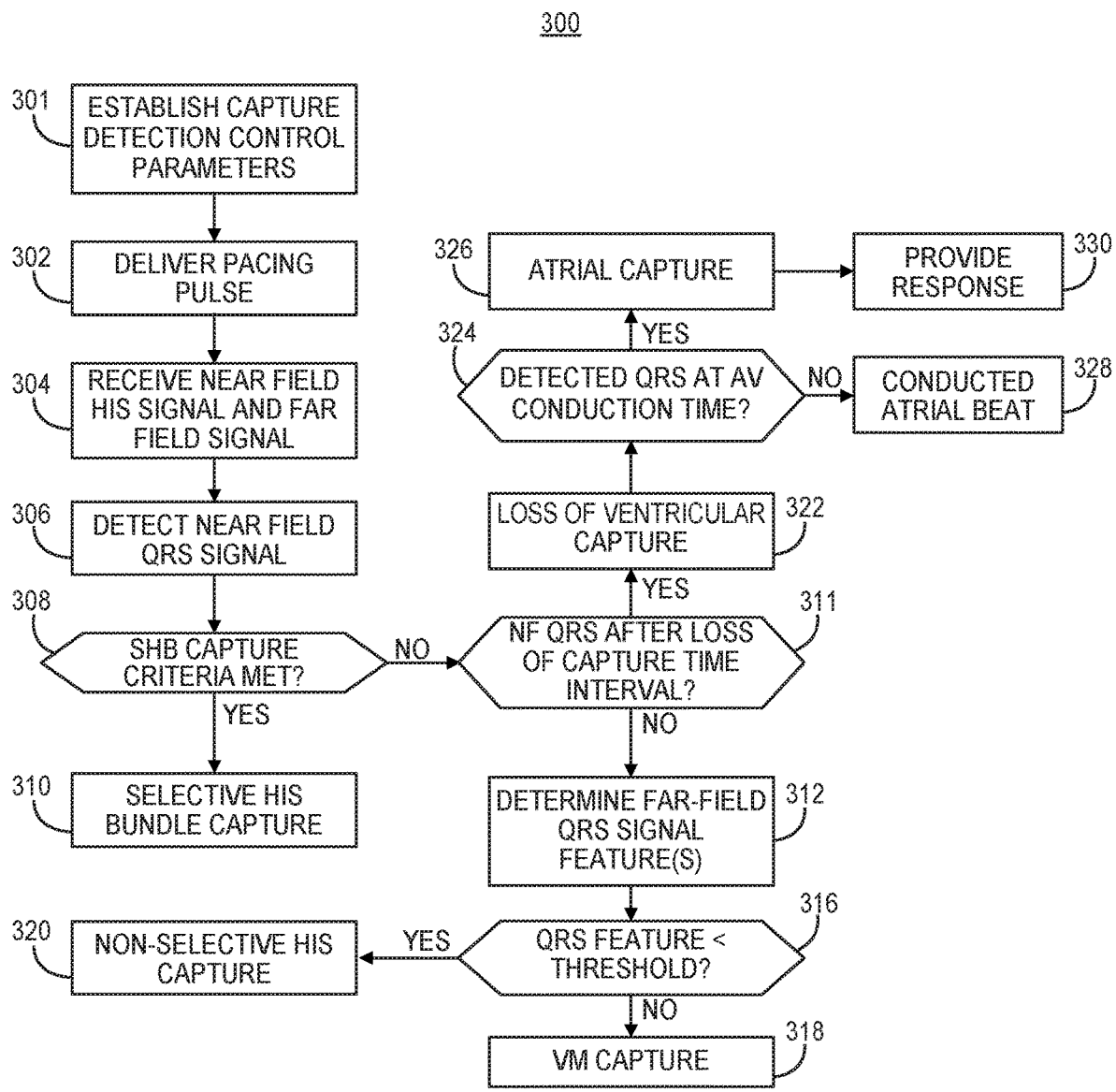
FIG. 5 is a flow chart of a method for determining a type of cardiac capture following a His bundle pacing pulse.

FIG. 5 is a flow chart 300 of a method, which may be performed by IMD 10 or intracardiac pacemaker 100, for determining a type of cardiac capture following a His bundle pacing pulse. In some examples, before starting capture detection, control circuit 80 may perform a set-up procedure for establishing control parameters that are used during His bundle capture detection. For instance, the process for establishing control parameters may be performed at block 301 to select the sensitivity setting for detecting QRS signals from the cardiac electrical signals received by sensing circuit 86 and/or for setting a capture detection window duration during which an evoked response signal caused by a delivered His bundle pacing pulse may be detected. The capture detection window is a time window that may be started upon delivery of a His bundle pacing pulse and extend for the capture detection window duration established at block 301.

In one example, control circuit 80 controls the therapy delivery circuit 84 to deliver dual chamber pacing including atrial pacing pulses delivered at an overdrive pacing rate and atrial synchronized His bundle pacing pulses, each delivered at an extended AV pacing interval after each respective atrial overdrive pacing pulse. The right atrium may be paced at a rate that is greater than an intrinsically sensed atrial rate, e.g., using RA lead 16 or atrial pacing electrodes included on pacemaker 100 if available. The intrinsic atrial rate may be determined by determining PP intervals, each measured as the time interval between two intrinsic (non-paced) P-waves consecutively sensed by sensing circuit 86. An atrial overdrive pacing rate may be set to 10 to 20 pulses per minute faster than the intrinsic rate, for example.

The extended AV pacing interval is set to a longer time interval than the AV pacing interval that is used to deliver His bundle pacing to promote optimal AV synchrony. The extended AV pacing interval may be set to 180 to 200 ms, for example, and the normal, non-extended AV pacing interval might be 50 to 150 ms and may be tailored to an individual patient. The atrial overdrive pacing with atrial synchronized His bundle pacing pulses delivered at an extended AV interval may be performed to establish a maximum capture detection window to reduce the likelihood of intrinsic AV conduction interfering with detection of evoked response R-wave signals during His bundle pacing.

As shown in FIG. 4, a time delay 220 occurs between a delivered His bundle pacing pulse 210 and the subsequent evoked response QRS signal 214 during SHB capture due to the time required for conduction along the His Purkinje conduction system. In order to detect SHB capture from the near field signal, a SHB capture detection time window may be set during which a detected QRS signal is determined to be evidence of SHB capture. The SHB capture detection window may be set to expire later than the expected time delay 220. If the SHB capture detection window ends too early, the evoked response signal 214 occurring at delay time 220 may be undersensed, leading to false loss of capture detection in some instances.

In some patients receiving His bundle pacing, however, intrinsic AV conduction may occur, causing an R-wave to be conducted from the atria following an intrinsic atrial P-wave or delivered atrial pacing pulse. The time for an intrinsic or paced atrial event to be conducted to the ventricles is referred to as the "AV conduction time." Depending on the AV conduction time, when a His bundle pacing pulse fails to capture, but AV conduction occurs, an intrinsically conducted R-wave arising from the AV conduction may be falsely sensed as an evoked response signal indicative of capture. In particular, since the AV conduction time may be only slightly longer than the time delay 220 during SHB capture, sensing an atrial conducted R-wave as an evoked response signal could lead to false SHB capture detection. Therefore if the SHB capture detection window is set too long, false SHB capture detection may occur due to intrinsic AV conduction. A capture threshold determined for SHB pacing based on false SHB capture detection will be underestimated. If the His bundle pacing pulse amplitude is set according to a capture threshold that is underestimated due to false SHB capture detection, the His bundle pacing therapy may not achieve the desired therapeutic benefit.

In order to establish a SHB capture detection window that promotes detection of SHB capture without falsely detecting conducted R-waves arising from atrial events conducted through the AV node, control circuit 80 may determine the AV conduction time during atrial overdrive pacing with atrial synchronized His bundle pacing at the extended AV pacing interval. The time interval between the delivered atrial pacing pulse and a subsequently detected QRS signal that occurs during the extended AV pacing interval may be determined as the AV conduction time.

Control circuit 80 may set a SHB capture detection window to be less than the AV conduction time, to avoid false capture detection due to sensing of atrial conducted ventricular depolarizations, but long enough to encompass the time delay 220 of SHB evoked response signals with a high probability. For example, if the AV conduction time is found to be 160 ms, the capture detection window may be set to 150 ms or less, e.g., 140 ms. If no AV conduction occurs or the AV conduction time is longer than the extended AV interval, no QRS signal is detected during the extended AV pacing interval. The His bundle pacing pulse is delivered at the extended AV pacing interval following each overdrive atrial pacing pulse. In this case, the capture detection window may be set as long as the extended AV interval.

Another example of a capture detection control parameter that may be established at block 301 by control circuit 80 may the sensitivity of R-wave detection circuitry of sensing circuit 86. As described in conjunction with FIG. 3, the sensitivity of R-wave detection circuitry is the lowest voltage amplitude of the cardiac electrical signal that may be detected as a QRS signal by sensing circuit 86. In some cases, far field P-waves may be present in the His bundle near field signal. The amplitude of the far field P-wave may exceed the sensitivity resulting in false evoked response QRS signal detection following a His bundle pacing pulse in some instances. At block 301, control circuit 80 may set a relatively low sensitivity voltage setting to increase the sensitivity of sensing circuit 86 to far field P-waves. The sensitivity may be se to 1.0 mV or less, 0.5 mV or less or other relatively low setting selected from the available sensitivity settings to determine if sensing of far field P-waves occurs.

With the sensitivity setting at a relatively low voltage, control circuit 80 may control therapy delivery circuit 84 to deliver atrial overdrive pacing with atrial synchronous His bundle pacing pulses at the extended AV pacing interval as described above. A QRS signal sensed from the near-field cardiac electrical signal during the extended AV interval may be an oversensed far-field P-wave, particularly if the signal is sensed relatively early during the extended AV interval. Thus, an early R-wave sensed event signal from near field sensing channel 87 may indicate an oversensed P-wave (evoked from the delivered atrial pacing pulse). False capture detection of a His bundle pacing pulse due to far field P-wave oversensing may lead to inaccurate capture pacing thresholds and pacing pulse amplitude selection in delivering effective His bundle pacing.

Control circuit 80 may detect a QRS signal by receiving an R-wave sensed event signal from sensing circuit 86. If an R-wave sensed event signal is received by control circuit 80 during the extended AV interval, control circuit 80 may identify the detected QRS signal as an oversensed far field P-wave. In response to an identified far field P-wave, control circuit 80 control sensing circuit 86 to adjust the sensitivity to a higher voltage setting to reduce the sensitivity of the R-wave detection circuitry to far-field P-wave over sensing.

Control circuit 80 may distinguish a received R-wave sensed event signal that is likely an oversensed far field P-wave from an R-wave sensed event signal that is likely an atrial conducted R-wave based on the relative timing of the R-wave sensed event signal during the extended AV pacing interval. For example, an R-wave sensed event signal within the first half of the extended AV pacing interval, or in the first 100 ms of the AV pacing interval, is likely to be a far field P-wave. An R-wave sensed event signal occurring relatively late in the extended AV pacing interval, for example in the second half of the extended AV pacing interval or after 100 ms of the AV pacing interval, is more likely to be an R-wave arising from AV conduction. An oversensed far field P-wave may additionally or alternatively be distinguished from a conducted R-wave based on the near field signal peak amplitude corresponding in time to the received R-wave sensed event signal. In some cases, a far field P-wave may have a lower amplitude than a conducted R-wave. As such, control circuit 80 may be configured to determine the timing and/or amplitude of a cardiac event signal sensed as an R-wave during the extended AV pacing interval and compare the timing and/or amplitude to criteria for discriminating far field P-waves from AV conducted R-waves.

In some examples, control circuit 80 may control sensing circuit 86 to decrease the sensitivity setting until far field P-waves are detected during the extended AV pacing interval. Sensing circuit 86 may adjust the sensitivity of at least near field sensing channel 87 used for sensing R-waves to a voltage setting that is greater than the highest sensitivity setting at which far-field P-waves are identified by control circuit 80 during the extended AV interval. In other examples, control circuit 80 may determine the peak voltage amplitude of the cardiac event of the near field signal that is identified as an oversensed far field P-wave. Control circuit 80 may set the sensitivity of sensing circuit 86 for sensing R-waves from the near-field cardiac electrical signal to a voltage that is a safety margin greater than the far-field P-wave peak amplitude. In still other examples, control circuit 80 may set the sensitivity to a selected setting and determine if far-field P-waves are sensed during the AV pacing interval. If no events are sensed during the AV pacing interval, oversensing of far-field P-waves is not expected to occur. A sensitivity setting that is equal to or greater than the tested sensitivity setting may be used for sensing R-waves from the near-field cardiac electrical signal for identification of evoked QRS signals by control circuit 80 for detecting capture by a His bundle pacing pulse.

In some examples, control circuit 80 controls telemetry circuit 88 to transmit the near field cardiac electrical signal to external device 50 for generating a display of the near field cardiac electrical signal and/or marker channel signals indicating the timing of sensed events relative to atrial and His bundle pacing pulses and the near field cardiac electrical signal. A user may authorize programming of selected control parameters, e.g., sensitivity for sensing R-waves and/or capture detection window duration, based on observation of the displayed signals and using the user interface of external device 50.

Accordingly, one control parameter used for capture detection and discrimination established at block 301 may be the sensitivity used by near field sensing channel 87 for sensing R-waves to avoid oversensing of far-field P-waves during capture detection. Another example of a control parameter that may be established during the setup procedure of block 301 is a capture detection window during which a sensed R-wave is an indication of an evoked response and capture by a His pacing pulse.

At block 302, the control circuit 80 starts the capture detection process by controlling therapy delivery circuit 84 to generate and deliver a His bundle pacing pulse. The His bundle pacing pulse may be delivered using a His lead, e.g., electrodes 32 and 34 of His lead 18 in the example of IMD 10 of FIG. 1. The His bundle pacing pulse may be delivered by an intracardiac pacemaker, e.g., using electrodes 102 and 104 of intracardiac pacemaker 100 of FIG. 2. The His bundle pacing pulse may or may not be synchronized to atrial events by an AV pacing interval.

At block 304, a His bundle near field signal and a far field cardiac electrical signal are received by sensing circuit 86. The His bundle near field signal may be received by the same electrodes used for delivering the His bundle pacing pulse, e.g., tip electrode 32 and ring electrode 34 (FIG. 1). In other examples, at least one electrode used for delivering the His bundle pacing pulse is used for sensing the His bundle near field signal, e.g., using the tip electrode 32 and housing 15. By using tip electrode 32, e.g., paired with the IMD housing 15, the evoked response to a His bundle pacing pulse that captures ventricular myocardial tissue will be conducted away from the pacing tip electrode 32 resulting in a greater likelihood of a negative polarity of the evoked QRS signal during VM capture and NSHB capture. The polarity of the evoked QRS signal when SHB capture occurs is expected to be positive. The polarity of the evoked QRS signal sensed during SHB capture, NSHB capture and VM capture using a selected near field sensing electrode vector may be established at the time of implant or follow up testing to verify that the polarity of the signal is a distinguishing feature between SHB capture (positive polarity) and other types of capture that includes ventricular myocardial tissue (NSHB and VM capture).

In the example of IMD 10 of FIG. 1, the far field signal may be received by a sensing electrode that excludes the electrodes used for delivering the His bundle pacing pulse. For instance, using the example of FIG. 1, the far field signal may be received using RA tip electrode 20 and housing 15, RA ring electrode 22 and housing 15, RV coil electrode 24 and housing 15, SVC coil electrode 26 and housing 15, RV tip electrode 28 and housing 15, or RV ring electrode 30 and housing 15. In other examples, RA tip electrode 20, RA ring electrode 22, RV tip electrode 28 or RV ring electrode 30 may be used in combination with either of RV coil electrode 24 or SVC coil electrode 26 to obtain a far field cardiac electrical signal. In the example of intracardiac pacemaker 100 of FIG. 2, the far field cardiac electrical signal may be received using housing based electrodes 104 and 106.

At block 306, the control circuit 80 detects the QRS signal following the delivered His bundle pacing pulse in the near field signal. In some examples, the near field QRS signal is detected by sensing circuit 86 based on a threshold crossing of the near field signal. A QRS detection signal may be passed to control circuit 80 from near field sensing channel 87. In other examples, control circuit 80 may receive a digital near field signal from sensing circuit 86 and determine the time of the QRS signal based on a threshold crossing, slew rate or other feature of the near field evoked response signal.

The control circuit 80 may compare the near field QRS signal to SHB capture criteria at block 308. The control circuit 80 may determine that SHB capture criteria are met by the near field QRS signal at block 308 in response to the time interval from the delivered His bundle pacing pulse to the time of the detected near field QRS signal being greater than an SHB time interval threshold but less than a loss of capture time interval threshold. For example, the time interval 220 from the His bundle pacing pulse to the time of detecting the near field QRS signal may be determined by the control circuit 80 and compared to a time interval threshold. The SHB time interval threshold may be set to at least 30 ms, at least 40 ms, or at least 50 ms in various examples and may be programmable for tailoring to an individual patient. A QRS signal detected earlier than the SHB time interval threshold is an indication of capture of myocardial cells and may be NSHB capture or VM capture.

In some instances, the His bundle pacing pulse may fail to capture both the His bundle and ventricular myocardial tissue, resulting in no ventricular evoked response following the His pacing pulse. A QRS signal may still occur, however, due to a conducted atrial beat, intrinsic or paced, if AV conduction is intact. The atrial depolarization may be conducted to the ventricles but may occur at a prolonged delay after the His bundle pacing pulse that failed to capture the ventricles. As such, the near field SHB capture criteria applied at block 308 may require that the QRS signal be detected within a time interval range, after a SHB time interval threshold but not later than a loss of capture time interval threshold. The ending time of the time interval range may be defined by the capture detection window established at block 301. The capture detection window may define the loss of capture time interval threshold following a His bundle pacing pulse. When a QRS signal is not sensed before the expiration of the capture detection window, loss of ventricular capture may be detected.

The SHB capture criteria applied to the near field QRS signal at block 308 may require that the near field QRS signal be detected after the SHB time interval threshold (and before a loss of capture time interval threshold), be a positive polarity signal, have a signal width less than a threshold width, have a signal area less than a threshold area, or any combination thereof. If the near field QRS signal satisfies the SHB capture criteria at block 308, the control circuit 80 detects SHB capture at block 310.

In response to the near field QRS signal not meeting the SHB capture criteria at block 308, e.g., the QRS signal occurs earlier than the SHB threshold time interval, has a negative polarity, a signal width greater than a threshold width, and/or a signal area greater than a threshold area, SHB capture is not detected. The process advances to block 311. If the near field (NF) QRS signal is detected after the loss of capture time interval threshold, control circuit 80 may detect loss of ventricular capture at block 322. The delivered His bundle pacing pulse may fail to capture both the His bundle and the ventricular myocardial tissue but may capture atrial tissue causing an atrial depolarization. If AV conduction is intact, the atrial depolarization may be conducted to the ventricles, and the resulting QRS signal may be detected from the His bundle near field signal. However, the QRS signal occurs at a prolonged delay, e.g., corresponding to the AV conduction time, and is evidence of loss of capture of the ventricles by the His pacing pulse. As such, loss of ventricular capture may be detected at block 322.

In some examples, the time from the His bundle pacing pulse to the detected QRS signal may be compared to an expected AV conduction time at block 324 in response to detecting loss of ventricular capture at block 322. Atrial capture may be suspected if the QRS signal is detected after a loss of capture time interval threshold and within a predetermined range of an approximate or expected AV conduction time required for an atrial depolarization to be conducted to the ventricles via the AV node. Atrial capture may be determined at block 326. If the QRS signal is detected at a time interval after the His bundle pacing pulse that is not within a range of an expected AV conduction time, an intrinsic atrial beat or an evoked atrial depolarization caused by an atrial pacing pulse, e.g., delivered by RA electrodes 20 and 22 of FIG. 1, may have been conducted to the ventricles. The detected QRS signal may be determined to be a conducted atrial beat at block 328.

If atrial capture is determined at block 326, an atrial capture response may be provided by control circuit 80 at block 330. The response may include reporting atrial capture by storing the event in memory 82 and transmitting a report of atrial capture to external device 50, generating an alert or alarm to the patient and/or clinician to notify the clinician that atrial capture is occurring and follow up is needed, and/or adjust His bundle pacing pulse control parameters or switch to ventricular pacing via a different pacing electrode vector, e.g., using electrodes carried by an RV lead 17 if present. In some cases, adjusting the pacing pulse amplitude, pacing pulse width, AV pacing interval, or other His bundle pacing control parameter may preclude atrial capture and enable His bundle and/or VM capture.

While not explicitly shown in FIG. 5, it is to be understood that if no QRS signal is detected at block 306 before a VV pacing interval expires, a backup His bundle pacing pulse may be delivered, e.g., at an increased pacing pulse energy. Control circuit 80 may set a VV pacing interval to provide backup ventricular pacing to prevent ventricular asystole, e.g., in a patient with complete AV block. In the example of FIG. 1, a backup ventricular pacing pulse may be provided by electrodes carried by RV lead 17.

If the SHB capture criteria are not met, and the detected QRS signal is not later than the loss of capture time interval threshold ("no branch of block 311), control circuit 80 may analyze the far field QRS signal at block 312 to determine if the QRS signal corresponds to a different type of capture. Control circuit 80 may receive a digitized far field signal from far field sensing channel 89 and determine one or more features of the far field QRS signal. One or more features of the far field QRS signal are compared to criteria for discriminating between NSHB capture and VM capture. For example, the far field QRS signal width and/or the QRS signal area may be determined at block 312. The evoked response signal during VM capture and the evoked response signal during NSHB capture may both occur relatively early after the His bundle pacing pulse and have the same polarity in both of the near field and far field signals. In the far field signal, however, the NSHB capture evoked response signal is expected to have a narrower signal width and/or smaller signal area than the VM capture evoked response signal.

Accordingly, at block 316, one or more far field QRS signal features are compared to NSHB capture criteria. The far field QRS signal width may be determined and compared to a NSHB width threshold and/or the far field QRS signal area may be determined and compared to a NSHB area threshold. If one or both of the far field QRS signal width and the far field QRS signal area are less than the respective width or area threshold, NSHB capture is detected at block 320. If the far field QRS signal feature(s) do not meet the NSHB capture criteria applied at block 316, VM capture is detected at block 318.

After determining the type of capture or determining loss of capture (e.g., at one of blocks 310, 318, 320, 322, 326 or 328) control circuit 80 may return to block 302 to continue monitoring the His bundle near field electrical signal and a far field cardiac electrical signal for providing capture monitoring on a beat-by beat or less frequent basis. In other examples, the process of FIG. 5 may be performed during a His bundle capture threshold test. Various examples of the applications of the capture determination methods of FIG. 5 are described below in conjunction with FIGS. 7-10.

Figure 6:
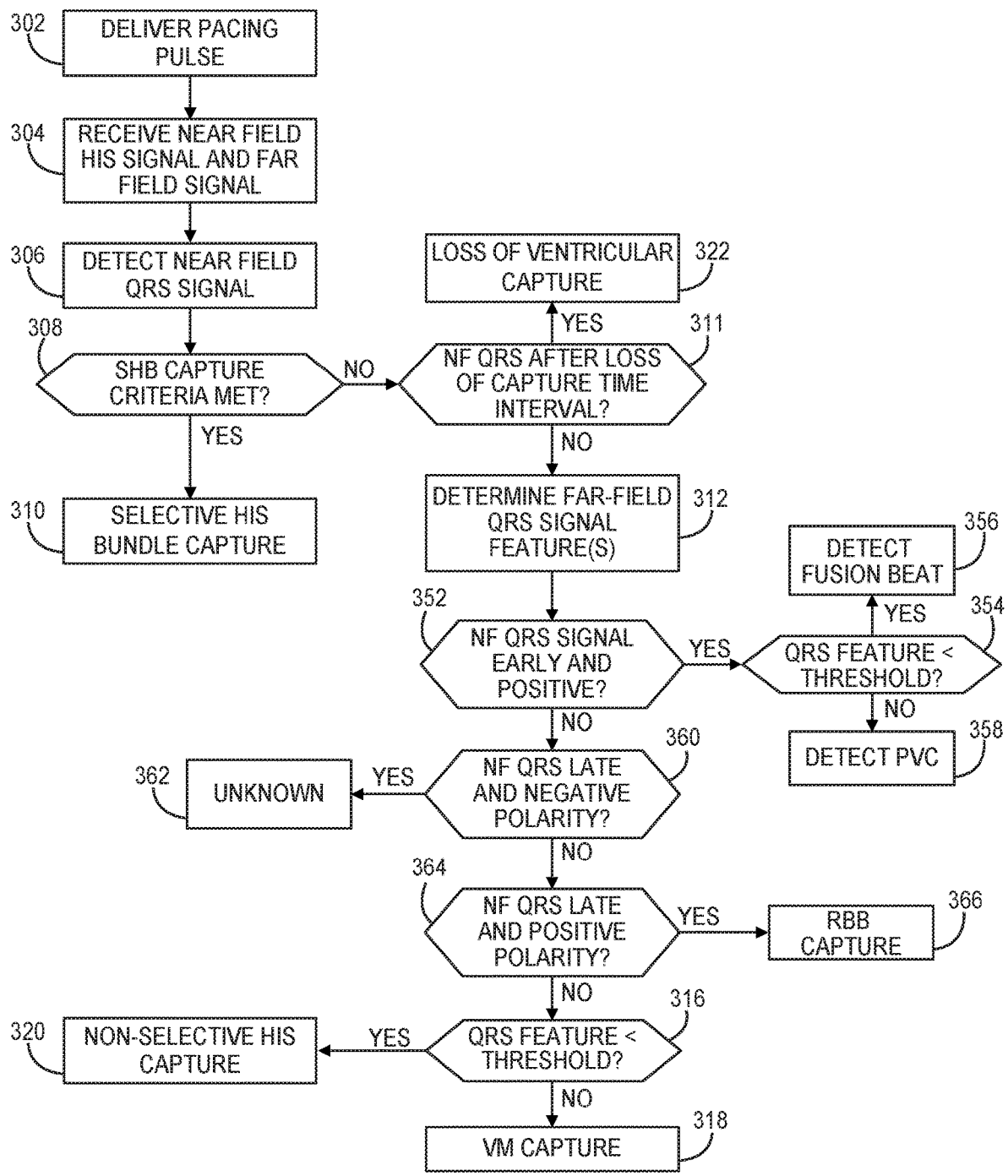
FIG. 6 is a flow chart of a method performed by an IMD for discriminating between different types of capture, loss of capture and other events following a His bundle pacing pulse according to another example.

FIG. 6 is a flow chart 350 of a method performed by an IMD for discriminating between different types of capture according to another example. In some cases, some but not all of the SHB capture criteria applied at block 308 of FIG. 5 may be satisfied. For example, the QRS signal may have a positive polarity but occur earlier than the SHB time interval threshold. In other instances, the QRS signal may be detected after the SHB time interval threshold but have a negative polarity. In such cases, SHB capture is not determined but the criteria for detecting NSHB capture criteria (e.g., a negative polarity QRS signal before the SHB time interval threshold and a narrow far field QRS signal width) or the VM capture criteria (e.g., a negative polarity QRS signal that occurs before the SHB time interval threshold and a wide far field QRS signal width) may not be satisfied either since some but not all SHB capture criteria were met. In these cases, the QRS signal may correspond to a fusion beat, a premature ventricular contraction (PVC), or selective capture of a bundle branch, e.g., the right bundle branch (RBB) without capturing the left bundle branch (LBB).

In the example of FIG. 6, additional criteria may be applied to the near field QRS signal and/or the far field QRS signal for discriminating between other types of capture or detecting other types of events. Identically numbered blocks in FIG. 6 correspond to like-numbered blocks shown in FIG. 5 and described above. If the SHB capture criteria are not met at block 308 and the near field QRS signal is not after the loss of capture time interval threshold ("no" branch of block 311), the QRS signal feature(s) are determined from the far field signal at block 312 as described above.

Decision blocks 352, 360 and 364 take into account situations when one of the SHB criteria are satisfied but not all. For example, if the near field QRS signal has a positive polarity but occurs early after the His bundle pacing pulse rather than after the SHB time interval threshold ("yes" branch of block 352), the QRS signal may represent a fusion beat or a PVC. A fusion beat and a PVC may be discriminated by comparing the far field QRS signal width and/or area at block 354. If the determined far field QRS signal width or area is greater than a respective width or area threshold, the early, positive polarity QRS signal is detected as a PVC at block 358. If the early, positive polarity QRS signal has a signal width and/or area that is less than the respective width or area threshold, a fusion beat is detected at block 356.

At block 360, control circuit 80 may account for the situation of the near field QRS signal being late, after the SHB time interval threshold but before the loss of capture time interval threshold, suggesting SHB capture but having a negative polarity instead of the expected positive polarity if SHB capture has occurred. If the near field QRS signal is after the SHB time interval threshold but has a negative polarity, the beat may be determined to be an unknown beat at block 362.

If the near field QRS signal is detected late, after the SHB time interval threshold but before the loss of capture time interval threshold, and has a positive polarity but didn't meet QRS signal width and/or area criteria for detecting SHB capture at block 308 ("yes" branch of block 364), right bundle branch capture (RBB capture) may be detected at block 366. In this case, a wide QRS signal is not consistent with SHB capture but a late occurring, positive QRS signal suggests the ventricular conduction system was captured by the His pacing pulse. Capture of the RBB causes the late, positive polarity QRS, and the wide QRS signal (or large QRS area) is evidence of conduction from the right to the left ventricle that takes longer than when the His bundle is captured and the depolarization is conducted to both the right and left bundle branches.

If the detected near field QRS signal is both early, before the SHB time interval threshold, and negative in polarity, the far field QRS signal feature(s) determined at block 312 (e.g., signal width and/or area) may be compared to a threshold at block 316 for discriminating between NSHB capture and VM capture as described above in conjunction with FIG. 5.

The techniques of FIGS. 5 and 6 for detecting a QRS signal following a His bundle pacing pulse and discriminating between at least SHB capture, NSHB capture, VM capture, and loss of capture (which may include determining atrial capture) may be used during a pacing capture threshold test, during capture monitoring during His bundle pacing, and/or during an IMD implant procedure for verifying acceptable electrode placement. Determination of the capture type following a QRS signal enables selection of pacing pulse parameters for achieving the desired capture type as further described below.

FIGS. 5 and 6 illustrate particular examples of criteria that may be applied for detecting different types of cardiac capture, loss of capture or other events from the near field His bundle electrical signal and the far field electrical signal. In Table I, an example truth table is shown listing example characteristics of the near field (NF) QRS signal and the far field (FF) QRS width that may be used to define criteria for detecting a variety of capture types and other events following a His bundle pacing pulse by analyzing the His bundle near field signal and the far field cardiac electrical signal. Based on these criteria, a variety of algorithms may be developed for detecting and discriminating different types of capture and other events that may occur following a His bundle pacing pulse. "Early" and "late" NF QRS time as listed in Table I may be defined as before or after, respectively, the SHB time interval threshold. "Very late" NF QRS time may be a QRS signal sensed after the loss of capture time interval threshold. "Narrow" and "wide" FF QRS width as listed in Table I may be defined as less than or greater than, respectively, a QRS width threshold. The actual criteria listed in Table I may vary between particular IMD systems and between patients, e.g., depending on IMD and electrode locations and other factors. The algorithms based on truth table criteria may include evaluating a feature of the His bundle near field signal to detect SHB capture followed by evaluating one or more features of the far field signal for determining the capture type if SHB capture is not detected.

TABLE I

Example "truth" table for establishing criteria for determining capture type and detecting loss of ventricular (LOV) capture and other events based on the near field (NF) QRS time (from the delivered His bundle pacing pulse), the near field QRS signal polarity, and the far field QRS signal width.

| EVENT | NF QRS time | NF QRS polarity | FF QRS width |
|---|---|---|---|
| NSHB capture | Early | negative | narrow |
| SHB capture | Late | positive | narrow |
| Fusion beat | Early | positive | narrow |
| PVC | Early | positive | wide |
| Unknown | Late | negative | narrow or wide |
| VM capture | Early | negative | wide |
| RBB capture | Late | positive | wide |
| LOV capture | very late | either | either |

Figure 7:
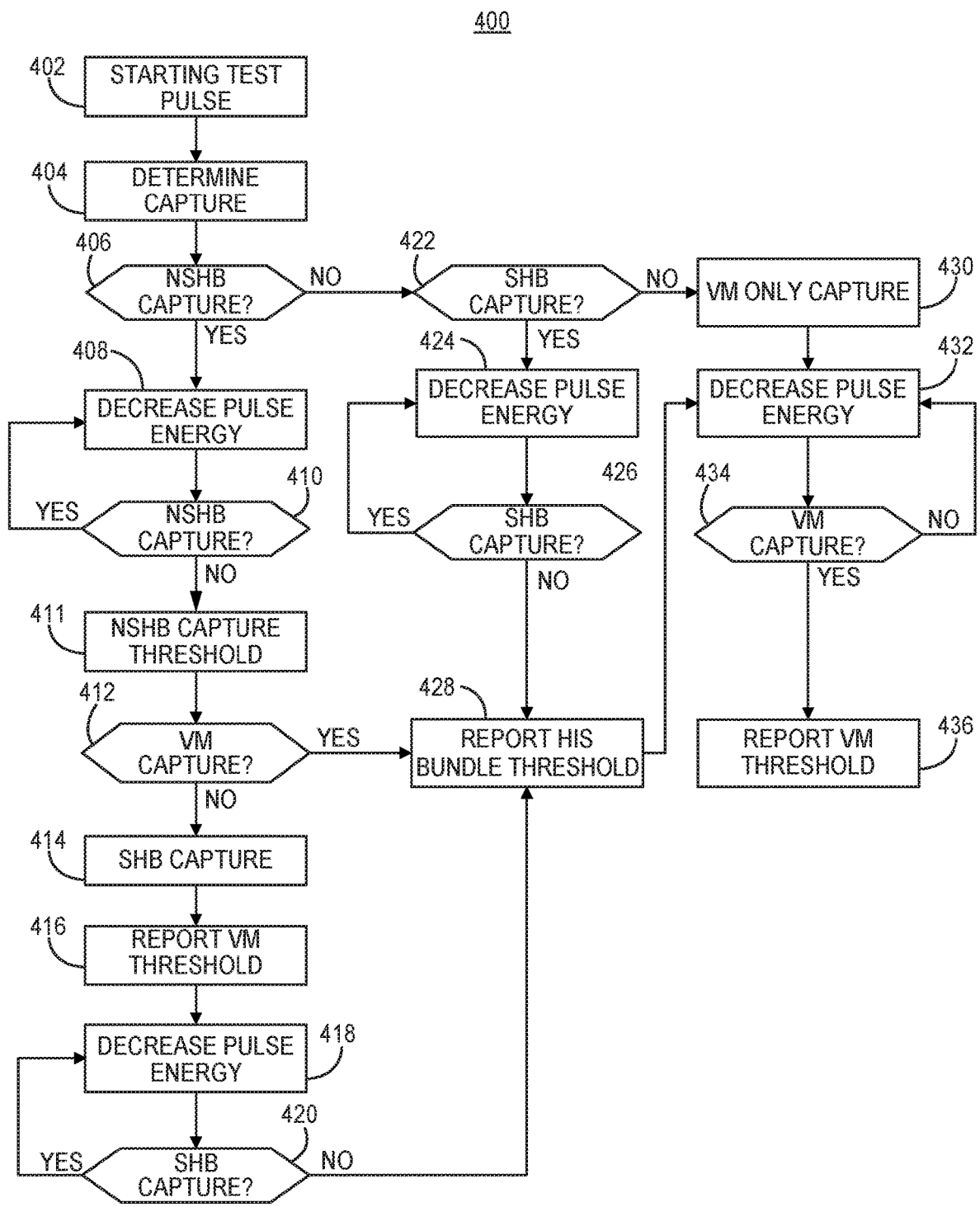
FIG. 7 is a flow chart for performing a capture threshold test for His bundle pacing according to one example.

FIG. 7 is a flow chart 400 for performing a threshold test for His bundle pacing according to one example. At block 402, the capture threshold test is started by delivering a His bundle pacing pulse at a test amplitude and test pulse width using a selected His bundle pacing electrode vector. The starting pacing pulse amplitude may be, with no limitation intended, up to 5.0 Volts, and the starting pulse width may be 0.4 ms or up to 1 ms. At block 404, capture is determined. The capture threshold test may be started with a relatively high pacing pulse energy such that ventricular capture is expected. It is to be understood that if loss of ventricular capture is detected, as described in conjunction with FIG. 5, the pulse energy may be increased to a higher starting test pulse energy.

In the example shown in FIG. 7, assuming ventricular capture occurs in response to the starting test pulse, ventricular capture is shown as being determined as one of SHB capture (block 422), NSHB capture (block 406), or VM capture (block 430). It is recognized however, that the additional criteria for detecting other types of capture or events, e.g., a fusion beat, PVC, RBB capture or an unknown signal, may be applied at block 404 in other examples. If a fusion beat, PVC, or unknown signal is detected at block 404, delivery of the starting test pulse may be repeated, possibly at a different pacing interval to avoid fusion and promote capture of the His bundle and/or the ventricular myocardium.

Capture may be determined at block 404 by analyzing both the His bundle near field signal and the far field cardiac electrical signal according to the techniques described above in conjunction with FIG. 5. In other examples, control circuit 80 may initially analyze the far field cardiac electrical signal to determine if NSHB capture is detected. For example, NSHB capture may be detected based on the far field signal evoked response signal occurring before the SHB time interval threshold and having a QRS signal width less than a width threshold and/or signal area that is less than an area threshold. NSHB capture may be further confirmed by analyzing the His bundle near field signal to verify that SHB capture detection criteria are not met.

If NSHB capture is detected as determined at decision block 406, control circuit 80 may be configured to automatically decrease the His bundle pacing pulse energy in a stepwise manner to determine the His bundle capture threshold and the VM capture threshold. The His bundle capture threshold may be greater than the VM capture threshold in some patients, and in other patients the VM capture threshold may be greater than the His bundle capture threshold. The His bundle capture threshold and the VM capture threshold may change over time in a given patient, for example, due changes in tissue encapsulation of the pacing electrode vector and/or or shifts in electrode location. As such, at one time the His bundle capture threshold may be higher than the VM capture threshold in a given patient, and at another time the VM capture threshold may be higher than the His bundle capture threshold. Accordingly, the threshold test of FIG. 7 may be performed to determine the two separate His bundle capture threshold and VM capture threshold. The higher one of the His bundle capture threshold and the VM capture threshold is also the NSHB capture threshold since both the His bundle and the ventricular myocardial tissue are being captured at the higher capture threshold.

At block 408, the pulse energy is decreased, for instance, by decreasing the pulse amplitude by 1.0 Volts, 0.5 Volts, 0.25 Volts, or other predetermined decrement. In other examples, the pacing pulse amplitude may be kept constant and the pacing pulse width may be decreased by one step decrement at block 408. For the sake of illustration, the threshold test described in conjunction with FIG. 7 is performed by decreasing the pacing pulse amplitude while keeping the pacing pulse width constant. However it is recognized that the threshold test may be performed by decreasing the pulse width given a fixed pulse amplitude, or a combination of pulse amplitude decrements and pulse width decrements may be used. Furthermore, while the threshold test is described as starting at a high pulse amplitude that is decreased in a stepwise manner, it is recognized that the threshold test may be performed by starting with a low pulse amplitude and increasing the pulse amplitude until the different types of capture are each identified, or a binary or other search algorithm may be used to adjust the His bundle pacing pulse energy to determine each of the His bundle capture threshold and the VM capture threshold.

Control circuit 80 determines if NSHB capture is still occurring at block 410 after the first decrease in the pacing pulse amplitude. If NSHB is detected at block 410, the pacing pulse energy continues to be decreased, e.g., by decreasing the pulse amplitude, until NSHB capture is no longer detected. If NSHB capture is no longer detected, the NSHB capture threshold is determined at block 411 as the lowest, preceding pacing pulse amplitude at which NSHB capture was detected. The His bundle pacing pulse at the current test amplitude and pulse width, at which NSHB capture was lost, may be capturing only the His bundle (SHB capture) or capturing only ventricular myocardial tissue (VM capture) but is no longer capturing both.

At block 412, control circuit 80 analyzes the His bundle near field signal and/or the far field cardiac electrical signal to determine if criteria for detecting SHB capture are satisfied or if criteria for detecting VM capture are satisfied after NSHB capture is no longer detected. Control circuit 80 may monitor the His bundle near field signal at block 410 and determine that NSHB capture is no longer occurring in response to detecting a near field evoked response signal that is later than the SHB time interval threshold and/or switched from being a negative polarity signal to a positive polarity signal. Based on the later near field evoked response signal and/or positive polarity evoked response signal indicating SHB capture, NSHB capture is no longer detected at block 410, and SHB capture is detected at block 414 ("no" branch of block 412). The NSHB capture threshold determined at block 411 is also reported as the VM capture threshold at bock 416 since VM capture was lost when NSHB capture was lost, leaving only SHB capture.

However, if a conversion from NSHB capture to SHB capture is not determined at block 412 based on analysis of the near field signal, control circuit 80 may analyze the far field signal to detect a loss of NSHB capture due to loss of His bundle capture, leading to VM capture. In another example, since NSHB capture was initially determined at block 406, control circuit 80 may monitor only the far field cardiac electrical signal at block 410 with each step decrease in His bundle pacing pulse amplitude to detect a loss in NSHB capture based on a change in the far field evoked response signal. For instance, if the far field evoked response signal becomes later in time following the His bundle pacing pulse or increases in signal width and/or area, control circuit 80 may determine that NSHB capture is no longer occurring at block 410. If the far field evoked response signal is still occurring early after the His bundle pacing pulse but is wider and/or increased in area, NSHB capture is not detected at block 410, and VM capture is detected at block 412.

In order to positively detect VM capture at block 412, control circuit 80 may compare the far field evoked response signal width and/or area to respective width and area thresholds set to predetermined values to distinguish VM capture from NSHB capture. If the far field evoked response signal is later in time at block 410, neither NSHB capture nor VM capture is detected at respective blocks 410 and 412. Control circuit 80 may perform additional analysis of the near field signal at block 414 to positively detect SHB capture based on criteria relating to the timing, polarity, width and/or area of the near field evoked response signal.

Capture of the His bundle is lost if VM capture is detected at block 412 after losing NSHB capture at block 410. The most recent His bundle pacing pulse amplitude and width that resulted in NSHB capture at block 410 is therefore the His bundle capture threshold. At block 428, control circuit 80 may report the His bundle capture threshold by storing the His bundle capture threshold in memory 82 and/or transmitting the His bundle capture threshold via telemetry circuit 88 for display on external device 50.

Control circuit 80 may advance to block 432 to control therapy delivery circuit 84 to decrease the His bundle pacing pulse amplitude until VM capture is lost at block 434. The lowest pacing pulse amplitude for the fixed pacing pulse width at which VM capture was still detected at block 434 is reported as the VM capture threshold at block 436.

In this case, a pacing pulse amplitude set to a value that is greater than or equal to the His bundle capture threshold results in NSHB pacing. A pacing pulse amplitude that is less than the His bundle capture threshold results in ventricular myocardial pacing. SHB capture may not be achievable without repositioning of the selected pacing electrode vector since the VM capture threshold is less than the His bundle capture threshold. The His bundle capture threshold is equal to the NSHB capture threshold in this situation of the His bundle capture threshold being greater than the VM capture threshold. If the His bundle capture threshold is not unacceptably high, NSHB pacing may be desired over ventricular myocardial pacing to provide conduction along the native conduction pathway. Furthermore, during NSHB pacing, even if His bundle capture is lost, VM capture may still be achieved to ensure that the patient does not experience ventricular asystole.

If VM capture is not detected after losing NSHB capture at block 410, SHB capture is detected at block 414. In this case, capture of the ventricular myocardial tissue is lost first as the pacing pulse amplitude is decreased. The VM capture threshold may be reported at block 416 as the lowest pulse amplitude at which NSHB capture was still detected, e.g., by storing the VM capture threshold in memory 82 and/or transmitting the VM capture threshold to external device 50. Control circuit 80 continues to control the therapy delivery circuit 84 to decrease the His bundle pacing pulse energy at block 418 until SHB capture is no longer detected at block 420. The His bundle capture threshold is the lowest pulse amplitude at which SHB capture was still detected. The His bundle capture threshold is reported at block 428. In this situation, SHB capture is achievable if the pacing pulse amplitude is set to be equal to or greater than the His bundle capture threshold but less than the VM capture threshold. NSHB capture may be desired, however, in order to reduce the likelihood of ventricular asystole. As such, the pacing pulse amplitude may be set higher than the VM capture threshold to promote NSHB pacing.

In some patients, depending on the local anatomy, electrode positioning or other factors, NSHB capture may not be detected in response to delivering the maximum pulse energy test pacing pulse at block 406. If SHB capture is detected following the first test pacing pulse at block 422, the highest pulse energy tested is below the VM capture threshold. The selected pacing electrode vector may be positioned such that only the His bundle is captured. Control circuit 80 may decrease the pacing pulse energy at block 424 until SHB capture is no longer detected at block 426, e.g., based on monitoring only the near field evoked response signal. At block 428, the His bundle capture threshold is reported as the lowest pulse amplitude at which SHB capture was still detected. In this case, the threshold search is complete since VM capture was never detected, so there is no VM capture threshold to determine and report.

If NSHB capture is not detected in response to the first, highest pacing pulse amplitude at block 406, VM capture may be detected at block 430 based on any of the example analyses of the His bundle near field and/or far field signals described above. If VM capture is detected at block 430, His bundle capture may not be achieved without relocating the His bundle pacing electrode vector. The pulse amplitude may be decreased at block 432 until VM capture is lost at block 434. The VM capture threshold amplitude may be reported at block 436 as the lowest pacing pulse amplitude at which VM capture was still detected. The determined and reported His bundle capture threshold, VM capture threshold and NSHB capture threshold corresponding to the higher one of the His bundle capture threshold and the VM capture threshold may be used by a clinician or by control circuit 80 to select a pacing pulse amplitude to achieve a desired type of capture.

Figure 8:
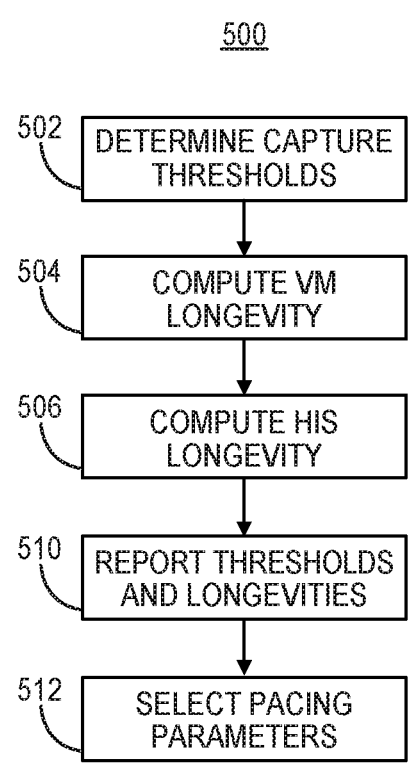
FIG. 8 is a flow chart of a method for determining IMD battery longevity and recommended pacing parameters based on His bundle capture threshold test results.

FIG. 8 is a flow chart 500 of a method for determining an expected IMD battery longevity and recommended pacing parameters based on His bundle capture threshold test results. At block 502, control circuit 80 may determine the His bundle capture threshold and the VM capture threshold using the techniques of FIG. 7. When both of the VM capture threshold and the His bundle capture threshold are determined, the higher one of the two is also the NSHB capture threshold. In some examples, the NSBH and VM capture types may not be distinguished.

At block 504, the expected battery longevity of the pacing device (e.g., IMD 10 or pacemaker 100) is computed based on pacing at, or a safety margin above, the VM capture threshold. The control circuit 80 may compute the expected battery longevity taking into account the remaining battery charge, an expected pacing burden based on historical data from the patient, the pacing pulse amplitude set to a programmed safety margin above the VM capture threshold, the programmed pacing pulse width and other pacing control parameters. At block 506, the expected battery longevity of the pacing device is determined by control circuit 80 based on pacing at a safety margin above the His bundle capture threshold.

At block 510, the capture thresholds and the expected battery longevity for pacing at a safety margin above the VM capture threshold and the expected battery longevity for pacing at a safety margin above the His bundle capture threshold are reported, e.g., by displaying the results on external device 50. The processor 52 of external device 50 may receive the determined capture thresholds and corresponding predicted battery longevities and generate a tabular, graphical, or textual display of the data. If the VM capture threshold is greater than the His bundle capture threshold, the device longevity for pacing at or above the VM capture threshold may correspond to the expected battery longevity if NSHB pacing is provided and is shorter than the expected battery longevity for SHB pacing. If the His bundle capture threshold is greater than the VM capture threshold, expected battery longevity for providing NSHB pacing may be less than providing VM only pacing. As such, in order to achieve NSHB pacing, the expected useful life of the pacing device may be shortened.

In some cases, NSHB pacing is desired to provide conduction of the evoked response along the normal conduction pathway with the assurance that if His bundle capture is lost VM capture may still occur. If the NSHB capture threshold (which may be equal to either the His bundle capture threshold or the VM capture, whichever is greater) is too high, the expected battery longevity of the pacing device may become unacceptably short. In the case of the VM capture being higher, the potential benefit of His bundle pacing with the assurance of backup VM capture in the case of losing His bundle capture may not outweigh the shortened functional lifetime of the pacing device. In this case, SHB pacing using a pulse amplitude that is less than the NSHB capture threshold may be preferred.

In the case of the His bundle capture threshold being greater than the VM capture threshold, ventricular pacing may be provided at a lower pacing pulse amplitude. VM pacing may be preferred in order to achieve a longer useful life of the pacing device when the SHB and corresponding NSHB capture threshold are substantially higher.

At block 512, the control circuit 80 (or external device 50) may select pacing parameters based on the capture thresholds and the corresponding expected battery longevities. In some examples, selected pacing parameters may be reported as recommended pacing parameters that are displayed on the external device 50. Display unit 54 of external device 50 may be a graphical user interface (GUI) that enables recommended pacing parameters and the associated capture thresholds and expected battery longevities to be displayed to a user and enable the user to accept a recommended setting such as pacing pulse amplitude or reject the recommended setting and select a different setting.

In other examples, the selected pacing parameters are automatically selected at block 512 by control circuit 80 for use in controlling therapy delivery circuit 84. Control circuit 80 may select the pacing parameters at block 512 by comparing the NSHB capture threshold (equal to either the His bundle capture threshold or the VM capture threshold, whichever is greater when both are determined) to a maximum pulse amplitude limit. If the NSHB capture threshold is less than the maximum limit (or the associated battery longevity is greater than a minimum battery longevity limit), the pacing pulse amplitude may be selected to be a safety margin above the NSHB capture threshold. His bundle pacing is provided with the assurance that VM capture is still provided if His bundle capture is lost.

If the His bundle capture threshold is less than the VM capture threshold, the pacing pulse amplitude may be selected at block 512 to be greater than the His bundle capture threshold but less than the VM capture threshold. SHB pacing may be provided using a lower pulse energy to conserve battery charge and provide the benefits of pacing the ventricles via the native conduction system.

Figure 9:
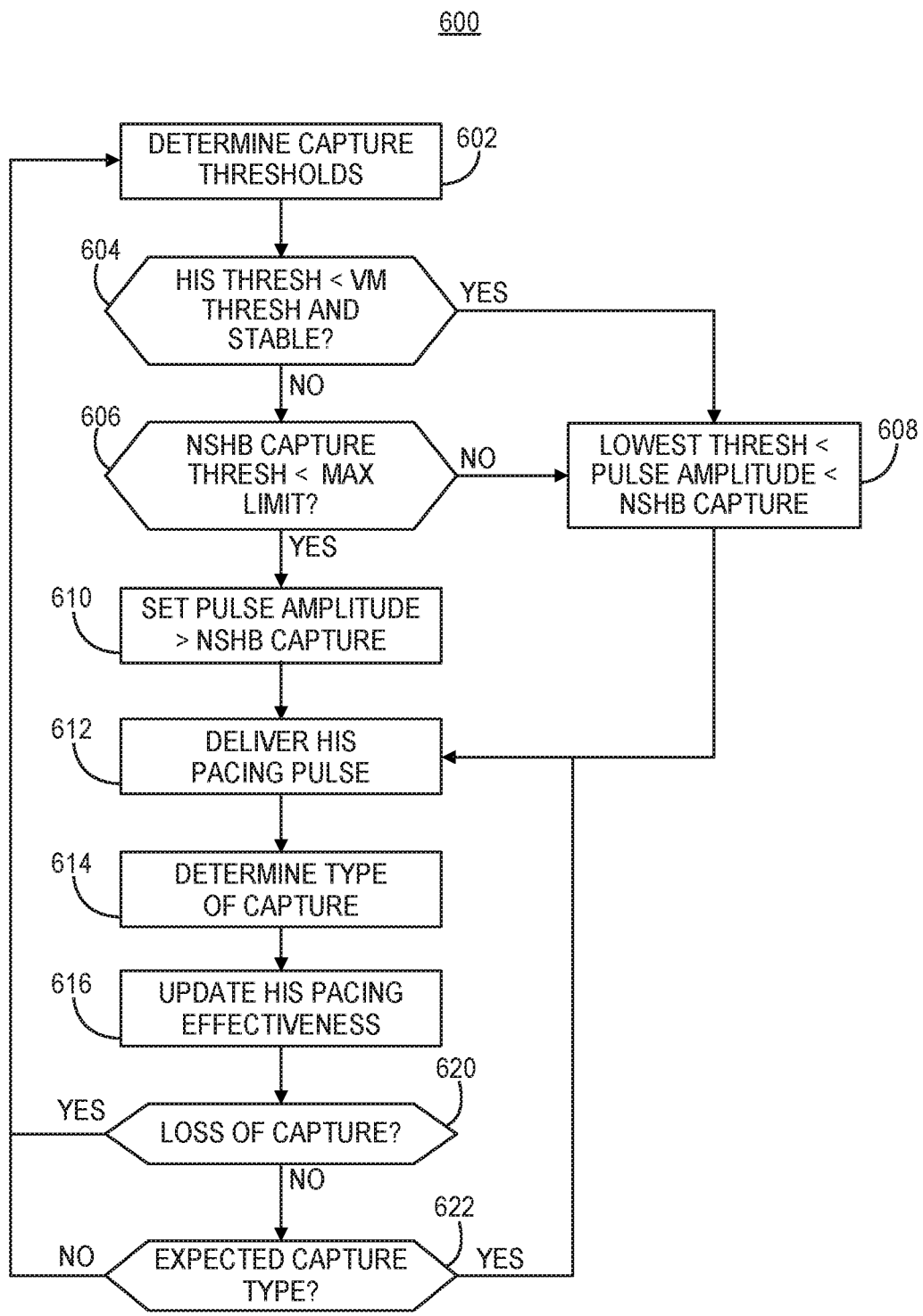
FIG. 9 is a flow chart of a method for capture monitoring during His bundle pacing according to one example.

FIG. 9 is a flow chart 600 of a method for capture monitoring during His bundle pacing according to one example. At block 602, the control circuit 80 may perform a capture threshold test to determine the His bundle capture threshold, the VM capture threshold, and the NSHB capture threshold equal to the greater one of the two. Control circuit 80 may determine whether the His bundle capture threshold is less than the VM capture threshold at block 602 and whether the His bundle capture threshold has been stable for one or more threshold tests. During a recovery period after initial implantation of the IMD system, inflammation and healing at the His bundle pacing electrode vector site may cause fluctuation in the capture thresholds. During an acute phase after surgery, NSHB pacing may be desired to provide His bundle pacing with the assurance that ventricular myocardial capture will occur if His bundle capture is lost. If the SHB capture threshold is stable and less than the VM capture threshold, however, SHB pacing may be desired to pace the ventricles via the native conduction system and conserve battery charge. As such, the type of pacing delivered (NSHB pacing, VM only pacing or SHB pacing) may be selected based on the capture thresholds and the stability of the His bundle capture threshold and taking into account the expected battery longevity of the IMD.

Control circuit 80 may determine that the His bundle capture threshold is stable based on a comparison of the current His bundle capture threshold to one or more previous His bundle capture thresholds. For example, if the His bundle capture threshold has not increased more than the programmed safety margin since the last capture threshold test (or a running average of two or more preceding His bundle capture thresholds), the His bundle capture threshold may be determined to be stable. If the His bundle capture threshold is stable and less than the VM capture threshold, the control circuit 80 may set the pacing pulse amplitude at block 608 to a safety margin, e.g., 0.25 to 0.5 Volts, greater than the His bundle capture threshold but less than the NSHB capture threshold (equal to the VM capture threshold in this case). SHB pacing is provided at block 612 based on the low, stable His bundle capture threshold.

If the His bundle capture threshold is greater than the VM capture threshold or unstable, however, NSHB pacing may be desired to promote VM capture if His bundle capture is lost. Accordingly, at block 606, control circuit 80 may compare the NSHB capture threshold to a maximum limit. An upper limit may be set to prevent excessive battery drain in the case of the NSHB capture threshold being unacceptably high. The maximum limit of the NSHB capture threshold may be set based on a minimum acceptable predicted battery longevity of the IMD. If the NSHB capture threshold is greater than the maximum limit, control circuit 80 may set the pacing pulse amplitude to a value less than the NSHB capture threshold at block 608. The pacing pulse amplitude may be set to a safety margin above the lower one of the His bundle capture threshold and the VM capture threshold. When the lower threshold is the His bundle capture threshold, a higher safety margin may be used to set the pacing pulse amplitude at block 608 to account for instability of the His bundle capture threshold. For example, the pacing pulse amplitude may be set to a multiple of the programmed safety margin if the His bundle capture threshold has been found to increase by more than the safety margin since the last capture threshold test. The multiple of the safety margin may be set based on how much the His bundle capture threshold has increased since a previous capture threshold test without causing the pulse amplitude to exceed the NSHB capture threshold (or other maximum pulse amplitude limit).

If the VM capture threshold is lower than the His bundle capture threshold at block 604 and the NSHB capture threshold is greater than a maximum limit at block 606, the pacing pulse amplitude may be set to a safety margin above the VM capture threshold and less than the NSHB (and His bundle) capture threshold at block 608. Ventricular myocardial pacing may be delivered until the His bundle capture threshold is lower and/or more stable.

If the His bundle capture threshold is greater than the VM capture threshold, or is instable but the NSHB capture threshold is less than the maximum limit (as determined at blocks 604 and 606), control circuit 80 may set the pacing pulse amplitude to a safety margin greater than the NSHB capture threshold at block 610. NSHB pacing may be desired until the His bundle threshold is lower than the VM threshold and is stable. In this case, the pacing pulse amplitude is set to a safety margin greater than the NSHB capture threshold at block 610. Providing NSHB pacing provides the assurance of VM capture when the His bundle capture is instable and/or higher than the VM capture threshold.

After setting the pacing pulse amplitude at block 608 or 610 to deliver the selected type of pacing (VM, SHB, or NSHB pacing) based on the determined capture thresholds, His pacing pulses are delivered at block 612 using the selected pacing pulse amplitude. At bock 614, control circuit 80 monitors His bundle pacing capture by determining the type of capture following a His bundle pacing pulse. Capture may be determined on a beat-by-beat basis, once per minute, once per hour, once per day or other scheduled basis. Capture determination may additionally occur on a triggered basis in response to a particular event or other sensor signal. The type of capture is determined at block 614 as one of at least SHB capture, NSHB capture or VM capture using the methods described above in conjunction with FIG. 5. In some instances, loss of capture may be determined at block 614 due to the pacing pulse amplitude falling below both the His bundle capture threshold and the VM capture threshold. In other examples, capture monitoring may include detecting other types of capture or events as described above in conjunction with FIG. 6.

After determining the type of capture (or loss of capture) at block 614, control circuit 80 may update a log stored in memory 82 that counts how often each type of capture is detected to provide a metric of effective His bundle pacing. The percentage or number of times that NSHB capture is detected, SHB capture is detected, and VM capture is detected (and optionally other types of capture or events) may be tracked and updated each time the type of capture is determined. This data may be transmitted to external device 50. Processor 52 may generate a display of the data for viewing by a clinician on display unit 54. Knowledge of the percentage of time that the His bundle is successfully being captured as opposed to ventricular myocardial pacing may provide useful diagnostic or prognostic information that is helpful in selecting pacing therapy parameters.

If loss of capture is detected, as determined at block 620, control circuit 80 may perform another capture threshold test by returning to block 602. If the type of capture that is expected is detected, control circuit 80 continues to deliver His pacing pulses according to the currently selected pacing control parameters (block 612) and monitoring capture (block 614) according to the capture monitoring protocol. The expected type of capture is based on the type of pacing and pacing pulse amplitude selected at block 608 or 610. For example, if the pacing pulse amplitude was set greater than the NSHB capture threshold, NSHB capture is expected. If the pacing pulse amplitude was set to be less than the NSHB capture threshold, then SHB capture or VM capture is expected, depending on which was found to have the lower capture threshold during the most recent capture threshold test.

If the type of capture detected is not the expected type of capture ("no" branch of block 622), one or both of the VM capture threshold and the His bundle capture threshold may have changed. Control circuit 80 may perform a new capture threshold test by returning to block 602. Based on the new capture threshold test results, the pacing pulse amplitude may be set differently to achieve a different type of capture. In this way, His bundle pacing is provided when the His bundle capture threshold is below a maximum acceptable limit (or the corresponding battery longevity is at least a minimum acceptable limit). Ventricular myocardial pacing is provided when the His bundle capture threshold is unacceptably high. NSHB pacing may be provided when the SHB capture threshold is higher than the VM capture threshold and/or instable but less than the maximum capture threshold limit.

Figure 10:
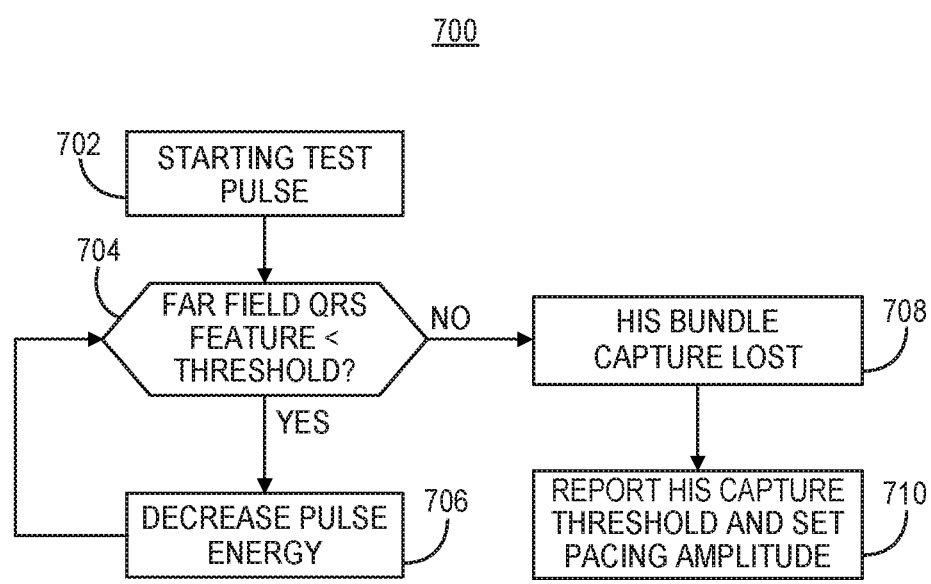
FIG. 10 is a flow chart of a method for performing a capture threshold test for His bundle pacing according to another example.

FIG. 10 is a flow chart 700 of a method for determining His bundle capture threshold according to another example. At block 702, a His bundle pacing pulse is delivered at a starting pulse energy using electrodes positioned for His bundle pacing. The starting pulse energy is set to be well above the expected His bundle capture threshold to promote a high likelihood of capturing the His bundle on the first test pulse.

At block 704, control circuit 80 determines a feature of the QRS signal from the far field cardiac electrical signal, such as the QRS width and/or QRS area. The determined feature is compared to a threshold at block 704 to determine if the far field QRS width and/or area are less than a threshold width and/or threshold area, respectively. If so, the relatively narrow QRS and/or small QRS area indicates that the His bundle is being captured, whether the capture type is SHB or NSHB capture. The control circuit 80 controls therapy delivery circuit 84 to decrease the His bundle pacing pulse energy at block 706, e.g., by reducing the pulse amplitude by a predetermined decrement. His pacing at the reduced pulse energy is delivered at block 704. This process continues until the far field QRS feature determined after a His pacing pulse delivered at a reduced pulse energy is greater than the threshold at block 704. If the far field QRS feature is greater than the threshold at block 704 ("no" branch), His capture is lost (block 708). A widening of the far field QRS signal and/or increased far field QRS signal area indicates that VM capture is occurring without capture of the His bundle.

At block 710 the His bundle capture threshold may be reported as the lowest pacing pulse energy applied before losing His bundle capture. Control circuit 80 may automatically set the His bundle pacing pulse energy at block 710 to a safety margin greater than the His bundle capture threshold. Additionally or alternatively, the control circuit 80 may report the His bundle capture threshold to a clinician by transmitting the capture threshold to external device 50 for display. In some clinical applications, pacing the His bundle is acceptable whether selective capture or non-selective capture of the His bundle is occurring. As such, discriminating only between VM capture and capture that includes His bundle capture, which may be either SHB or NSHB capture, is all that may be required for selecting a pacing pulse control parameters to promote His bundle pacing.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of circuits or components associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a pacemaker has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. An implantable medical device system, comprising:
   a sensing circuit configured to:
      receive a near field His bundle electrical signal via a first sensing electrode vector, and
      receive a far field cardiac electrical signal via a second sensing electrode vector that is different than the first sensing electrode vector;
   a therapy delivery circuit configured to generate His bundle pacing pulses delivered to a patient's heart via a His pacing electrode vector; and
   a control circuit configured to:
      determine a type of cardiac capture evoked by a His bundle pacing pulse delivered by the therapy delivery circuit by:
         detecting a near field QRS signal from the near field His bundle electrical signal following the His bundle pacing pulse;
         determining a time interval from the His bundle pacing pulse to the near field QRS signal;
         comparing the time interval to a first time interval threshold;
         in response to the time interval being less than the first time interval threshold, determining a feature of the far field cardiac electrical signal;
         comparing the far field cardiac electrical signal feature to a non-selective His bundle capture threshold;
         determining the type of cardiac capture as being non-selective His bundle capture that includes capture of both of a His bundle and ventricular myocardium in response to at least the far field cardiac electrical signal feature being less than the non-selective His bundle capture threshold; and
         determining the type of cardiac capture as being only ventricular myocardial capture in response to at least the far field cardiac electrical signal feature being greater than the non-selective His bundle capture threshold.

2. The system of claim 1, wherein the control circuit is further configured to:
   determine the type of cardiac capture as being selective His bundle capture that includes capture of only the His bundle in response to the time interval being greater than the first time interval threshold.

3. The system of claim 1, wherein the control circuit is further configured to:
   compare the time interval to a second time interval threshold greater than the first time interval threshold; and
   determine loss of ventricular capture in response to the time interval being greater than the second time interval threshold.

4. The system of claim 1, wherein the control circuit is further configured to:
   compare the time interval to an expected atrioventricular conduction time range; and
   detect atrial capture in response to the time interval being in the expected atrioventricular conduction time range.

5. The system of 4, wherein the control circuit is further configured to provide an atrial capture response in response to detecting atrial capture, the atrial capture response comprising at least one of:
   adjusting a ventricular pacing control parameter; and
   generating an atrial capture notification.

6. The system of claim 1, wherein the control circuit is further configured to:
   control the therapy delivery circuit to deliver a plurality of His bundle pacing pulses comprising a plurality of pacing pulse energies;
   determine a non-selective His bundle capture threshold from among the plurality of pacing pulse energies based on QRS signals detected from at least the far field cardiac electrical signal following each one of the plurality of His bundle pacing pulses; and
   control the therapy delivery circuit to deliver non-selective His bundle pacing pulses each having a pacing pulse energy greater than the non-selective His bundle capture threshold.

7. The system of claim 1, wherein the control circuit is further configured to:
compare the determined type of cardiac capture to an expected type of cardiac capture; and
in response to the determined type of cardiac capture being different than the expected type of cardiac capture, perform a capture threshold test.

8. The system of claim 1, wherein the control circuit is further configured to perform a His bundle capture threshold test by:
controlling the therapy delivery circuit to deliver a plurality of His bundle pacing pulses comprising a plurality of pacing pulse energies;
determining the type of capture as being non-selective His bundle capture following at least one of the plurality of His bundle pacing pulses;
determining a non-selective His bundle capture threshold as a lowest one of the plurality of pacing pulse energies for which the type of capture is determined to be non-selective His bundle capture;
determining a first one of ventricular myocardial capture and selective His bundle capture evoked by one of the plurality of His bundle pacing pulses delivered at a next lower one of the plurality of pacing pulse energies that is less than the non-selective His bundle capture threshold;
determining a loss of the second one of the ventricular myocardial capture and selective His bundle capture in response to determining the first one of ventricular myocardial capture and selective His bundle capture evoked by the next lower one of the plurality of pacing pulse energies;
determining a second capture threshold for the second one of the ventricular myocardial capture and selective His bundle capture as being equal to the non-selective His bundle capture threshold; and
determining a first capture threshold for the first one of the ventricular myocardial capture and selective His bundle capture as being a lowest one of the plurality of pacing pulse energies evoking the first one of the ventricular myocardial capture and selective His bundle capture.

9. The system of claim 8, wherein the control circuit is further configured to:
select a pacing type from a plurality of pacing types comprising at least non-selective His bundle pacing and selective His bundle pacing based on the first capture threshold and the second capture threshold; and
set at least one of a pacing pulse amplitude and a pacing pulse width based on the selected pacing type.

10. The system of claim 1, wherein the control circuit is further configured to:
determine a non-selective His bundle capture threshold;
compare the non-selective His bundle capture threshold to a maximum limit; and
control the therapy delivery circuit to deliver His bundle pacing pulses having a pacing pulse energy that is greater than the non-selective His bundle capture threshold in response to the non-selective His bundle capture threshold being less than the maximum limit.

11. The system of claim 10, wherein the control circuit is further configured to:
control the therapy delivery circuit to deliver one of ventricular myocardial pacing and selective His bundle pacing comprising His bundle pacing pulses having a pacing pulse energy that is less than the non-selective His bundle capture threshold in response to the non-selective His bundle capture threshold being greater than the maximum limit.

12. The system of claim 1, further comprising a power source including at least one battery;
wherein the control circuit is further configured to:
determine a pacing capture threshold that includes His bundle capture;
determine an expected battery longevity based on the pacing capture threshold;
compare the expected battery longevity to a minimum longevity; and
control the therapy delivery circuit to deliver His bundle pacing using a pacing pulse energy greater than the pacing capture threshold that includes His bundle capture in response to the expected battery longevity being greater than the minimum longevity.

13. The system of claim 1, further comprising:
an implantable power source including at least one battery;
an implantable telemetry circuit; and
an external device comprising a processor, an external telemetry circuit, and a display unit;
wherein the control circuit is further configured to:
determine a His bundle pacing capture threshold;
determine a ventricular myocardial pacing capture threshold;
determine an expected battery longevity corresponding to each of the His bundle pacing capture threshold and the ventricular myocardial pacing capture threshold; and
transmit the determined expected battery longevities to the external device;
wherein the processor generates a display on the display unit comprising the expected battery longevities.

14. The system of claim 13, wherein the control circuit is configured to:
select a pacing pulse amplitude in response to the determined expected battery longevities; and
at least one of deliver His bundle pacing pulses using the selected pacing pulse amplitude or display the selected pacing pulse amplitude on the display unit.

15. The system of claim 1, wherein:
the therapy delivery circuit is configured to deliver a plurality of His bundle pacing pulses comprising a plurality of pacing pulse energies;
the control circuit is further configured to:
determine a type of cardiac capture evoked by each of the plurality of pacing pulses;
based on the type of cardiac capture evoked by each of the plurality of His bundle pacing pulses, determine a first selective His bundle capture threshold corresponding to capture of only the His bundle and a non-selective His bundle capture threshold corresponding to capture of the His bundle and ventricular myocardium;
compare the first selective His bundle capture threshold to at least one previously determined selective His bundle capture threshold;
detect selective His bundle capture threshold instability in response to the comparison; and
the therapy delivery circuit is configured to deliver His bundle pacing pulses using a first pacing pulse energy that is greater than the non-selective His bundle capture threshold in response to the control circuit detecting the selective His bundle capture threshold instability.

16. The system of claim 15, wherein:
the control circuit is configured to:
- determine a second selective His bundle capture threshold after determining the first selective His bundle capture threshold;
- compare the second selective His bundle capture threshold to at least the first His bundle capture threshold; and
- detect selective His bundle capture threshold stability in response to the comparison; and the therapy delivery circuit is configured to deliver His bundle pacing pulses using a second pacing pulse energy that is greater than the selective His bundle capture threshold and less than the non-selective His bundle capture threshold in response to the control circuit detecting the His bundle capture threshold stability.

17. The system of claim 1, wherein the control circuit is further configured to:
- determine a QRS polarity from the His bundle near field signal; and
- determine the type of cardiac capture evoked by the His bundle pacing pulse based on the time interval, the QRS polarity, and the far field cardiac electrical signal feature as one of: non-selective His bundle capture, ventricular myocardial capture, selective His bundle capture, selective bundle branch capture, atrial capture, fusion, and loss of ventricular capture.

18. The system of claim 1, wherein:
- the therapy delivery circuit is configured to deliver an atrial overdrive pacing pulse and start an atrioventricular pacing interval following the atrial overdrive pacing pulse;
- the sensing circuit is configured to a set a sensitivity voltage setting for sensing the near field QRS signal;
- the control circuit is configured to identify an oversensed far field P wave in response to the near field His bundle electrical signal exceeding the sensitivity voltage setting during the atrioventricular pacing interval; and
- the sensing circuit is configured to increase the sensitivity voltage setting in response to the control circuit identifying the oversensed far field P wave.

19. The system of claim 1, wherein:
the therapy delivery circuit is configured to deliver an atrial overdrive pacing pulse;
the sensing circuit is configured to detect a conducted QRS signal from the near field His bundle electrical signal after the atrial overdrive pacing pulse;
the control circuit is configured to:
- determine an atrioventricular conduction time extending from the atrial overdrive pacing pulse to the conducted QRS signal;
- set a second time interval threshold based on the atrioventricular conduction time; and
- determine the type of cardiac capture as being selective His bundle capture that includes capture of only the His bundle in response to the time interval from the His bundle pacing pulse to the near field QRS signal being greater than the first time interval threshold and less than the second time interval threshold.

20. A method, comprising:
receiving by a sensing circuit of an implantable medical device a near field His bundle electrical signal via a first sensing electrode vector;
receiving a far field cardiac electrical signal by the sensing circuit via a second sensing electrode vector different than the first sensing electrode vector;
generating His bundle pacing pulses delivered to a patient's heart via a His pacing electrode vector; and
determining a type of cardiac capture evoked by a His bundle pacing pulse delivered by the therapy delivery circuit by:
- detecting a near field QRS signal from the near field His bundle electrical signal following the His bundle pacing pulse;
- determining a time interval from the His bundle pacing pulse to the near field QRS signal;
- comparing the time interval to a first time interval threshold;
- in response to the time interval being less than the first time interval threshold, determining a feature of the far field cardiac electrical signal;
- comparing the far field cardiac electrical signal feature to a non-selective His bundle capture threshold;
- determining the type of cardiac capture as being non-selective His bundle capture that includes capture of both of a His bundle and ventricular myocardium of the patient's heart in response to at least the far field cardiac electrical signal feature being less than the non-selective His bundle capture threshold; and
- determining the type of cardiac capture as being only ventricular myocardial capture in response to at least the far field cardiac electrical signal feature being greater than the non-selective His bundle capture threshold.

21. The method of claim 20, further comprising:
determining the type of cardiac capture as being selective His bundle capture that includes capture of only the His bundle in response to the time interval being greater than the first time interval threshold.

22. The method of claim 20, further comprising:
comparing the time interval to a second time interval threshold greater than the first time interval threshold; and
determining loss of ventricular capture in response to the time interval being greater than the second time interval threshold.

23. The method of claim 20, further comprising:
comparing the time interval to an expected atrioventricular conduction time range; and
detecting atrial capture in response to the time interval being in the expected atrioventricular conduction time range.

24. The method of 23, further comprising providing an atrial capture response in response to detecting atrial capture, the atrial capture response comprising at least one of:
adjusting a ventricular pacing control parameter; and
generating an atrial capture notification.

25. The method of claim 20, further comprising:
delivering a plurality of His bundle pacing pulses comprising a plurality of pacing pulse energies;
determining a non-selective His bundle capture threshold from among the plurality of pacing pulse energies based on QRS signals detected from at least the far field cardiac electrical signal following each one of the plurality of His bundle pacing pulses; and
delivering non-selective His bundle pacing pulses each having a pacing pulse energy greater than the non-selective His bundle capture threshold.

26. The method of claim 20, further comprising:
comparing the determined type of cardiac capture to an expected type of cardiac capture; and in response to the determined type of cardiac capture being different than the expected type of cardiac capture, perform a capture threshold test.

27. The method of claim 20, further comprising performing a capture threshold test by:
delivering a plurality of His bundle pacing pulses comprising a plurality of pacing pulse energies;
determining the type of capture as being non-selective His bundle capture following at least one of the plurality of His bundle pacing pulses;
determining a non-selective His bundle capture threshold as a lowest one of the pacing pulse energies for which the type of capture is determined to be non-selective His bundle capture is determined;
determining a first one of ventricular myocardial capture and selective His bundle capture evoked by one of the plurality of His bundle pacing pulses delivered at a next lower one of the plurality of pacing pulse energies that is less than the non-selective His bundle capture threshold;
determining a loss of the second one of the ventricular myocardial capture and selective His bundle capture in response to determining the first one of ventricular myocardial capture and selective His bundle capture evoked by the next lower one of the plurality of pacing pulse energies;
determining a second capture threshold for the second one of the ventricular myocardial capture and selective His bundle capture as being equal to the non-selective His bundle capture threshold; and
determining a first capture threshold for the first one of the ventricular myocardial capture and selective His bundle capture as being a lowest one of the plurality of pacing pulse energies evoking the first one of the ventricular myocardial capture and selective His bundle capture.

28. The method of claim 27, further comprising:
selecting a pacing type from a plurality of pacing types comprising at least non-selective His bundle pacing and selective His bundle pacing based on the first capture threshold and the second capture threshold; and
selecting at least one of a pacing pulse amplitude and a pacing pulse width based on the selected pacing type.

29. The method of claim 20, further comprising:
determining a non-selective His bundle capture threshold;
comparing the non-selective His bundle capture threshold to a maximum limit; and
delivering His bundle pacing pulses having a pacing pulse energy that is greater than the non-selective His bundle capture threshold in response to the non-selective His bundle capture threshold being less than the maximum limit.

30. The method of claim 29, further comprising:
delivering one of ventricular myocardial pacing and selective His bundle pacing comprising His bundle pacing pulses having a pacing pulse energy that is less than the non-selective His bundle capture threshold in response to the non-selective His bundle capture threshold being greater than the maximum limit.

31. The method of claim 20, further comprising:
determining a pacing capture threshold that includes His bundle capture;
determining an expected battery longevity based on the pacing capture threshold;
comparing the expected battery longevity to a minimum longevity; and
delivering His bundle pacing using a pacing pulse energy greater than the pacing capture threshold that includes His bundle capture in response to the expected battery longevity being greater than the minimum longevity.

32. The method of claim 20, further comprising:
determining a His bundle pacing capture threshold;
determining a ventricular myocardial pacing capture threshold;
determining an expected battery longevity corresponding to each of the His bundle pacing capture threshold and the ventricular myocardial pacing capture threshold; and
transmitting the determined expected battery longevities to an external device;
generating a display on a display unit of the external device comprising the expected battery longevities.

33. The method of claim 32, further comprising:
selecting a pacing pulse amplitude in response to the determined expected battery longevities; and
at least one of delivering His bundle pacing pulses using the selected pacing pulse amplitude and displaying the selected pacing pulse amplitude on the display unit.

34. The method of claim 20, further comprising:
delivering a plurality of His bundle pacing pulses comprising a plurality of pacing pulse energies;
determining a type of cardiac capture evoked by each of the plurality of pacing pulses;
based on the type of cardiac capture evoked by each of the plurality of His bundle pacing pulses, determining a first selective His bundle capture threshold corresponding to capture of only the His bundle and a non-selective His bundle capture threshold corresponding to capture of the His bundle and ventricular myocardium;
comparing the first selective His bundle capture threshold to at least one previously determined selective His bundle capture threshold;
detecting selective His bundle capture threshold instability in response to the comparison; and
delivering His bundle pacing pulses using a first pacing pulse energy that is greater than the non-selective His bundle capture threshold in response to detecting the selective His bundle capture threshold instability.

35. The method of claim 34, further comprising:
determining a second selective His bundle capture threshold after determining the first selective His bundle capture threshold;
comparing the second selective His bundle capture threshold to at least the first His bundle capture threshold;
detecting selective His bundle capture threshold stability in response to the comparison; and
delivering His bundle pacing pulses using a second pacing pulse energy that is greater than the selective His bundle capture threshold and less than the non-selective His bundle capture threshold in response to detecting the His bundle capture threshold stability.

36. The method of claim 20, further comprising:
determining a QRS polarity from the His bundle near field signal; and
determining the type of cardiac capture evoked by the His bundle pacing pulse based on the time interval, the QRS polarity, and the far field cardiac electrical signal feature as one of: non-selective His bundle capture, ventricular myocardial capture, selective His bundle capture, selective bundle branch capture, atrial capture, fusion, and loss of ventricular capture.

37. The method of claim 20, further comprising:
delivering an atrial overdrive pacing pulse;
setting an atrioventricular pacing interval following the atrial overdrive pacing pulse;
setting a sensitivity voltage setting for sensing the near field QRS signal;
identifying an oversensed far field P wave in response to the near field His bundle electrical signal exceeding the sensitivity voltage setting during the atrioventricular pacing interval; and
increasing the sensitivity voltage setting for detecting the near field QRS signal in response to identifying the oversensed far field P wave.

38. The method of claim 20, further comprising:
delivering an atrial overdrive pacing pulse;
detecting a conducted QRS signal from the near field His bundle electrical signal after the atrial overdrive pacing pulse;
determining an atrioventricular conduction time extending from the atrial overdrive pacing pulse to the conducted QRS signal;
setting a second time interval threshold based on the atrioventricular conduction time; and
determining the type of cardiac capture as being selective His bundle capture that includes capture of only the His bundle in response to the time interval from the His bundle pacing pulse to the near field QRS signal being greater than the first time interval threshold and less than the second time interval threshold.

39. A non-transitory, computer-readable storage medium comprising a set of instructions which, when executed by a controller of an implantable medical device (IMD), cause the IMD to:
receive a near field His bundle electrical signal produced by a patient's heart via a first sensing electrode vector;
receive a far field cardiac electrical signal produced by the patient's heart via a second sensing electrode vector different than the first sensing electrode vector;
generate His bundle pacing pulses delivered to the patient's heart via a His pacing electrode vector; and
determine a type of cardiac capture evoked by a delivered His bundle pacing pulse by:
detecting a near field QRS signal from the near field His bundle signal following the His bundle pacing pulse;
determining a time interval from the His bundle pacing pulse to the near field QRS signal;
comparing the time interval to a first time interval threshold;
in response to the time interval being less than the first time interval threshold, determining a feature of the far field cardiac electrical signal;
comparing the far field cardiac electrical signal feature to a non-selective His bundle capture threshold;
determining the type of cardiac capture as being non-selective His bundle capture that includes capture of both of a His bundle and right ventricular myocardium of the patient's heart in response to at least the far field cardiac electrical signal feature being less than the non-selective His bundle capture threshold; and
determining the type of cardiac capture as being ventricular myocardial capture in response to at least the far field cardiac electrical signal feature being greater than the non-selective His bundle capture threshold.

\* \* \* \* \*